United States Patent [19]

Wexler

[11] Patent Number: 4,609,397

[45] Date of Patent: Sep. 2, 1986

[54] HERBICIDAL 3-[[(4,6-DIMETHOXYPYRIMIDINE-2-YL)AMINOCARBONYL]AMINOSULFONYL-METHYL]-1,5-DIMETHYL-1H-PYRAZOLE-4-CARBOXYLIC ACIDS, ETHYL ESTERS

[75] Inventor: Barry A. Wexler, Wilmington, Del.

[73] Assignee: E. I. Du Pont de Nemours and Company, Wilmington, Del.

[21] Appl. No.: 679,145

[22] Filed: Dec. 11, 1984

Related U.S. Application Data

[63] Continuation-in-part of Ser. No. 581,817, Feb. 21, 1984, abandoned.

[51] Int. Cl.[4] .................. A01N 43/48; C07D 403/00; C07D 239/00; C07D 405/14
[52] U.S. Cl. .......................................... 71/92; 71/88; 71/90; 71/93; 544/212; 544/213; 544/253; 544/320; 544/331; 546/268; 546/270; 546/271; 546/276; 546/283; 548/262; 548/263; 548/268; 548/336; 548/342; 548/374; 548/378; 549/59; 549/60; 549/62; 549/63; 549/74; 549/396; 549/434; 549/435
[58] Field of Search ............... 544/320, 331; 71/92; 548/374, 378, 376

[56] References Cited

U.S. PATENT DOCUMENTS

| 4,127,405 | 11/1978 | Levitt | 71/93 |
|---|---|---|---|
| 4,169,719 | 10/1979 | Levitt | 71/92 |
| 4,221,585 | 9/1980 | Levitt | 71/92 |
| 4,302,241 | 11/1981 | Levitt | 71/92 |
| 4,348,220 | 9/1982 | Schwing | 71/92 |
| 4,398,939 | 8/1983 | Levitt | 71/90 |
| 4,420,325 | 12/1983 | Sauers | 71/92 |
| 4,435,206 | 3/1984 | Levitt | 71/92 |
| 4,481,029 | 11/1984 | Levitt | 71/93 |

FOREIGN PATENT DOCUMENTS

| 87780 | 9/1983 | European Pat. Off. . |
| 95925 | 12/1983 | European Pat. Off. . |
| 59-13778 | 1/1984 | Japan . |
| 833850 | 5/1983 | South Africa . |

*Primary Examiner*—Donald G. Daus
*Assistant Examiner*—Cecilia Shen

[57] ABSTRACT

Pyrazole sulfonylureas are useful as pre- and post-emergence herbicides. Typical of this group is 3-[[(4,6-dimethoxypyrimidin-2-yl)aminocarbonyl]aminosulfonylmethyl]-1,5-dimethyl-1H-pyrazole-4-carboxylic acid, ethyl ester.

21 Claims, No Drawings

HERBICIDAL 3-[[(4,6-DIMETHOXYPYRIMIDINE-2-YL)AMINOCARBONYL]AMINOSULFONYLMETHYL]-1,5-DIMETHYL-1H-PYRAZOLE-4-CARBOXYLIC ACIDS, ETHYL ESTERS

BACKGROUND OF THE INVENTION

This invention relates to novel pyrazole sulfonylureas which are useful as pre- and post-emergence herbicides. The compounds of this invention and their agriculturally suitable salts, are useful as agricultural chemicals such as herbicides.

U.S. Pat. Nos. 4,169,719 and 4,127,405 disclose herbicidal benzene and thiophene sulfonamides.

U.S. Pat. No. 4,435,206 discloses herbicidal pyridine sulfonamides.

U.S. Pat. No. 4,420,325 discloses benzyl sulfonylureas such as:

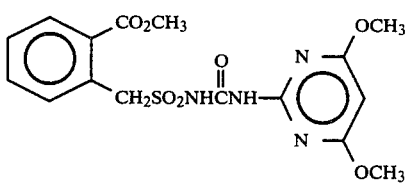

EP-A-No.87780 (published Sept. 7, 1983), filed by Nissan Chemical Industries discloses pyrazole sulfonamides of the general formula shown below.

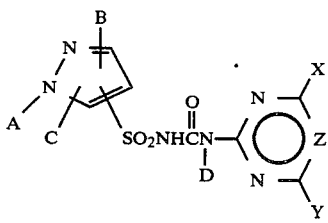

wherein
A is H, $C_1$–$C_8$ alkyl or optionally substituted phenyl;
B and C are independently H, halogen, $NO_2$, $C_1$–$C_8$ alkyl, $CO_2R$, etc.;
D is H or $C_1$–$C_8$ alkyl;
Z is CH or N; and
X and Y are methyl, methoxy, etc.

The presence of undesired vegetation causes substantial damage to useful crops, especially agricultural products that satisfy mans' basic food and fiber needs, such as cotton, rice, corn, wheat and the like. The current population explosion and concomitant world food and fiber shortage demand improvements in the efficiency of producing these crops. Preventing or minimizing loss of a portion of such valuable crops by killing or inhibiting the growth of undesired vegetation is one way of improving this efficiency.

A wide variety of materials useful for killing or inhibiting (controlling) the growth of undesired vegetation is available; such materials are commonly referred to as herbicides.

SUMMARY OF THE INVENTION

This invention relates to novel compounds of Formula I, agriculturally suitable compositions containing them and their method-of-use as pre-emergent or post-emergent herbicides or as plant growth regulators.

$$JSO_2NHCNA \underset{R}{|} \quad \overset{O}{\underset{\|}{}} \qquad I$$

wherein

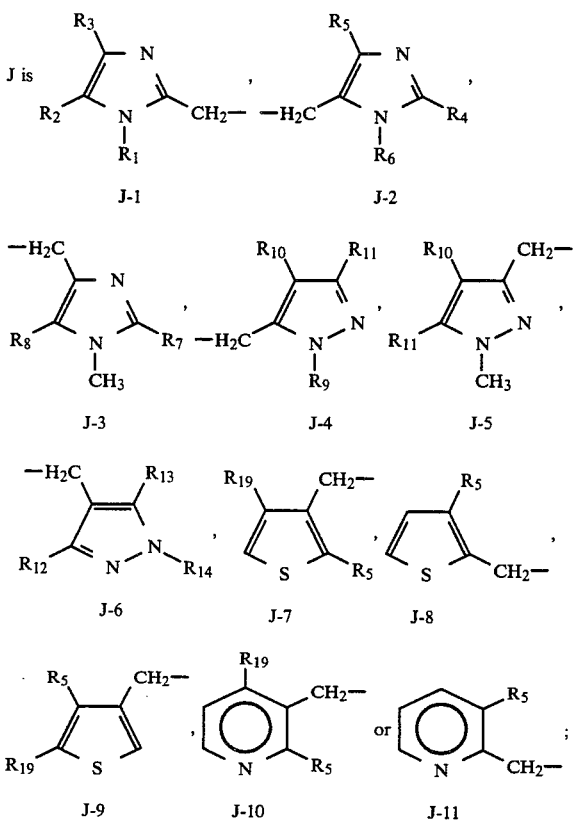

R is H or $CH_3$;
$R_1$ is H, $C_1$–$C_3$ alkyl, $CO_2R_{15}$, $SO_2NR_{16}R_{17}$ or $SO_2R_{18}$;
$R_2$ is H or $CH_3$;
$R_3$ is H or $CH_3$;
$R_4$ is H or $CH_3$;
$R_5$ is H, $CH_3$, Cl, Br, $CO_2R_{15}$, $C(O)NR_{16}R_{17}$, $SO_2NR_{16}R_{17}$, $SO_2N(OCH_3)CH_3$, $SO_2R_{18}$ or $NO_2$;
$R_6$ is H, $C_1$–$C_3$ alkyl, $CO_2R_{15}$, $SO_2NR_{16}R_{17}$ or $SO_2R_{18}$;
$R_7$ is H or $CH_3$;
$R_8$ is $CO_2R_{15}$, $C(O)NR_{16}R_{17}$, $SO_2NR_{16}R_{17}$, $SO_2N(OCH_3)CH_3$, $SO_2R_{18}$ or $NO_2$;
$R_9$ is H, $C_1$–$C_3$ alkyl or phenyl;
$R_{10}$ is $CO_2R_{15}$, $C(O)NR_{16}R_{17}$, $SO_2NR_{16}R_{17}$, $SO_2N(OCH_3)CH_3$, $SO_2R_{18}$ or $NO_2$;
$R_{11}$ is H or $CH_3$;
$R_{12}$ is H, $CO_2R_{15}$, $C(O)NR_{16}R_{17}$, $SO_2NR_{16}R_{17}$, $SO_2N(OCH_3)CH_3$, $SO_2R_{18}$ or $NO_2$;
$R_{13}$ is H, $CO_2R_{15}$, $C(O)NR_{16}R_{17}$, $SO_2NR_{16}R_{17}$, $SO_2N(OCH_3)CH_3$, $SO_2R_{18}$ or $NO_2$;
$R_{14}$ is H or $CH_3$;
$R_{15}$ is $C_1$–$C_2$ alkyl;
$R_{16}$ is H or $C_1$–$C_2$ alkyl;
$R_{17}$ is H or $C_1$–$C_2$ alkyl;

$R_{18}$ is $C_1$–$C_2$ alkyl;
$R_{19}$ is H, $CH_3$, Cl, Br, $NO_2$, $C_1$–$C_2$ alkylthio or $C_1$–$C_2$ alkylsulfonyl;
A is

A-1, A-2, A-3, A-4, A-5, A-6

X is $CH_3$, $OCH_3$, Cl, Br, $OCH_2CF_3$ or $OCHF_2$;
Y is $C_1$–$C_3$ alkyl, $CH_2F$, cyclopropyl, C≡CH, $OCH_3$, $OC_2H_5$, $CH_2OCH_3$, $NH_2$, $NHCH_3$, $N(CH_3)_2$, $OCH_2CH_2F$, $CF_3$, $SCH_3$, $OCH_2CH=CH_2$, $OCH_2C\equiv CH$, $OCH_2CH_2OCH_3$, $CR(OCH_3)_2$, $CR(OCH_2CH_3)_2$ or $OCF_2H$;
Z is CH or N;
$X_1$ is $CH_3$, $OCH_3$, $OC_2H_5$ or $OCF_2H$;
$Y_1$ is O or $CH_2$;
$X_2$ is $CH_3$, $C_2H_5$ or $CH_2CF_3$;
$Y_2$ is $OCH_3$, $OC_2H_5$, $SCH_3$, $SC_2H_5$, $OCF_2H$, $SCF_2H$, $CH_3$ or $CH_2CH_3$;
$X_3$ is $CH_3$ or $OCH_3$;
$Y_3$ is H or $CH_3$;
provided that
  (1) when X is Cl or Br, then Z is CH and Y is $OCH_3$, $OC_2H_5$, $NHCH_3$, $N(CH_3)_2$ or $OCF_2H$;
  (2) $R_5$ and $R_6$ are not simultaneously H;
  (3) when $R_6$ is other than H or $C_1$–$C_3$ alkyl, then $R_5$ must be H;
  (4) $R_{12}$ and $R_{13}$ are not simultaneously H;
  (5) when $R_{12}$ is other than H, then $R_{13}$ must be H;
  (6) when X or Y is $OCF_2H$, then Z is CH;
  (7) $R_5$ and $R_{19}$ are not simultaneously H; and
  (8) when J is J-8 or J-11 then $R_5$ is other than H.

Preferred for their higher herbicidal activity, greater plant growth regulant activity and/or more favorable ease of synthesis are:
  (1) Compounds of Formula I where
    R is H;
    A is A-1;
    X is $CH_3$ or $OCH_3$; and
    Y is $C_1$–$C_2$ alkyl or $C_1$–$C_2$ alkoxy.
  (2) Compounds of Preferred 1 where J is J-1.
  (3) Compounds of Preferred 2 where J is J-4.
  (4) Compounds of Preferred 3 where J is J-5.
  (5) Compounds of Preferred 4 where J is J-6.

Specifically preferred for their highest herbicidal activity, greatest plant growth regulant activity and/or more favorable ease of synthesis are:

3-[[(4,6-dimethoxypyrimidin-2-yl)aminocarbonyl]aminosulfonylmethyl]-1,5-dimethyl-1H-pyrazole-4-carboxylic acid, ethyl ester, m.p. 180°–183° C.; and 5-[[(4,6-dimethoxypyrimidin-2-yl)aminocarbonyl]aminosulfonylmethyl]-1,3-dimethyl-1H-pyrazole-4-carboxylic acid, ethyl ester, m.p. 190° C.

DETAILED DESCRIPTION OF THE INVENTION

Synthesis

The compounds of Formula I can be prepared by one or more of the methods described below in Equations 1, 2, 3 and 4.

As shown in Equation 1, compounds of Formula I can be prepared by reacting a sulfonyl isocyanate of Formula II with an appropriate heterocyclic amine of Formula III. J, R and A are as previously defined.

Equation 1

$$JSO_2N=C=O + \underset{R}{HN}-A \longrightarrow I$$
$$\text{II} \qquad\qquad \text{III}$$

The reaction is carried out at 25° to 100° C. in an inert, aprotic solvent such as methylene chloride or xylene for 0.5 to 24 hours as taught in U.S. Pat. No. 4,127,405.

Compounds of Formula I, where $R_1$, $R_5$, $R_6$, $R_8$, $R_{10}$, $R_{12}$ and $R_{13}$ of J are other than $CO_2R_{15}$, can be prepared by reacting the sulfonamides of Formula IV with an appropriate methyl carbamate of Formula V in the presence of at least an equimolar amount of trimethylaluminum, as shown in Equation 2.

Equation 2

$$JSO_2NH_2 + CH_3O\overset{O}{\overset{\|}{C}}NH-A \xrightarrow[CH_2Cl_2]{AlMe_3} I$$
$$\text{IV} \qquad\qquad \text{V}$$

The reaction is carried out at 25° to 40° C. in a solvent such as methylene chloride for 10 to 96 hours under an inert atmosphere as taught in EPO No. 84,244 (published July 27, 1983). The required carbamates V are prepared by reacting the corresponding amines III with dimethylcarbonate or methyl chloroformate in the presence of a strong base.

Alternatively, compounds of Formula I, can be prepared by reacting a sulfonylcarbamate of Formula VI with an appropriate amine of Formula III, as shown in Equation 3.

Equation 3

$$JSO_2NH\overset{O}{\overset{\|}{C}}OC_6H_5 + III \longrightarrow I$$
$$\text{VI}$$

The reaction is carried out at 50° to 100° C. in a solvent such as dioxane for 0.5 to 24 hours as taught in EPO publication No. 44807. The required carbamates VI are prepared by reacting the corresponding sulfonamides IV with diphenylcarbonate in the presence of a strong base.

Additionally, compounds of Formula I, can be prepared by reacting a sulfonamide of Formula IV with an appropriate heterocyclic phenyl carbamate of Formula VII, in the presence of a nonnucleophilic base, such as 1,8-diazabicyclo[5.4.0]undec-7-ene (DBU) as shown below in Equation 4.

Equation 14

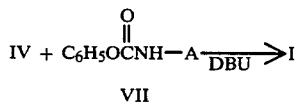

The reaction is carried out at 20° to 100° C. in an inert solvent, such as dioxane, for 0.5 to 24 hours by the methods taught in EPO publication No. 44807. The required carbamates, VII, are prepared by reacting the corresponding heterocyclic amines, III, with phenylchloroformate in the presence of a base.

The intermediate sulfonyl isocyanates of Formula II in Equation 1 can be prepared as shown in Equations 5 and 6.

As shown in Equation 5, sulfonyl isocyanates of Formula II where J is other than $J_1$, $J_2$ and $J_3$ can be prepared by the reaction of sulfonamides of Formula IV with phosgene, in the presence of n-butyl isocyanate and a tertiary amine catalyst, such as diazabicyclo[2.2.2]octane (DABCO ®), at reflux in a solvent such as xylene by the method of U.S. Pat. No. 4,238,621.

Equation 5

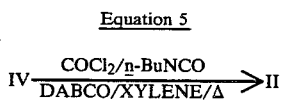

The sulfonyl isocyanates can also be prepared from the sulfonamides by a two step procedure involving (a) reacting the sulfonamides with n-butyl isocyanate in the presence of a base such as $K_2CO_3$ at reflux in an inert solvent such as 2-butanone forming a n-butyl sulfonylurea; and (b) reacting this compound with phosgene and a tertiary amine catalyst at reflux in xylene solvent. The method is similar to a procedure taught by Ulrich and Sayigh, *Newer Methods of Preparative Organic Chemistry*, Vol. VI, p. 223–241, Academic Press, New York and London, W. Foerst Ed.

Alternatively, as shown in Equation 6, the sulfonyl isocyanates of Formula II can be prepared by reacting the corresponding sulfonyl chlorides VIII with cyanic acid salts.

Equation 6

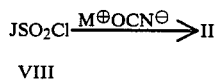

The reaction is carried out at 25° to 100° C. in an inert aprotic solvent such as acetonitrile for 0.5–24 hours in the presence of phosphorus pentoxide and an alkali metal salt such as lithium iodide according to the teachings of Japanese Patent No. 76/26,816 (*Chem. Abst.*, 85:77892e (1976)).

As shown in Equation 7, sulfonamides of Formula IV can be prepared from the corresponding sulfonyl chlorides of Formula VIII by contacting with either anhydrous or aqueous ammonia.

Equation 7

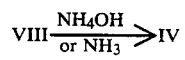

The preparation of sulfonamides from sulfonyl chlorides is widely reported in the literature, for reviews see: F. Hawking and J. S. Lawrence, "The Sulfonamides," H. K. Lewis and Co., London, 1950 and E. H. Northey, "The Sulfonamides and Allied Compounds," Reinhold Publishing Corp., New York, 1948.

The requisite methylsulfonyl chlorides of Formula VIII may be synthesized from appropriately substituted benzylic type chlorides or benzylic type bromides, IX, by the two-step sequence of reactions outlined below in Equation 8 and Equation 9.

Equation 8

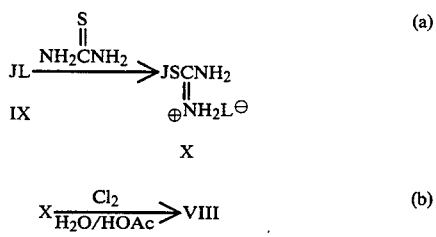

wherein
L is Cl or Br; and
J is as previously defined.

Equation 9

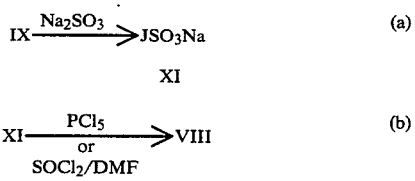

Equation 8(a)

The conversion of alkyl halides to isothiouronium salts is well precedented in the chemical literature. For relevant examples, see T. B. Johnson and J. M. Sprague, *J. Am. Chem. Soc.*, 58, 1348 (1936); ibid, 59, 1837 and 2439 (1937); ibid, 61, 176 (1939). In a typical procedure, a benzylic type halide of Formula IX is treated with thiourea in protic solvents such as methanol or ethanol, or aprotic solvents such as methylene chloride or benzene. Temperatures of 40°–80° over one-half to 24 hours are typically required to complete the reaction. The product salts, X, are isolated by cooling and filtration or by concentration to remove the solvent. The salts, X, are generally sufficiently pure to be carried on directly to step (8b) without further purification.

Equation 8(b)

The oxidative chlorination of isothiouronium salts to afford sulfonyl chlorides is most efficiently carried out according to the procedure of Johnson as described in *J. Am. Chem. Soc.*, 61, 2548 (1939). Thus, the salts of Formula X (L=chlorine or bromine) are dissolved or suspended in water or aqueous acetic acid and treated with at least three equivalents of chlorine at temperatures between 5°-20° C. When the hydrobromide salts X (L=bromine) are used, it is sometimes advantageous to exchange the bromide ion for nitrate ion before chlorination by treatment with an aqueous solution of one equivalent of silver nitrate; the precipitated silver bromide is removed by filtration and the filtrate treated as described above. The product sulfonyl chlorides are isolated either by simple filtration or extraction into a suitable solvent such as methylene chloride or n-butyl chloride followed by drying and evaporation of the combined organic extracts. No further purification of the sulfonyl chlorides, VIII, is necessary.

The conversion of a benzylic type chloride or bromide of Formula IX to a sulfonic acid salt of Formula XI as shown in Equation 9(a) is well known in the art. For a review, see Gilbert "Sulfonation and Related Reactions" Interscience Publishers, New York, 1965, pp. 136–148 and 161–163. The methods of conversion of a sulfonic acid salt of Formula XI to a sulfonyl chloride of Formula VIII is well known to those skilled in the art.

Benzylic type bromides of Formula IXa (L=bromine) may be prepared as shown below in Equation 10 by treating the appropriate methyl imidazole or pyrazole XII, with N-bromosuccinimide (NBS).

Equation 10

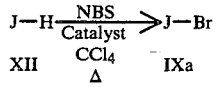

wherein Q is as previously defined.

The reaction represented in Equation 10 can be most conveniently effected by heating a solution of the methyl imidazole or pyrazole derivatives, XII, and N-bromosuccinimide in a suitable solvent such as carbon tetrachloride at reflux temperature. A free radical catalyst such as azoisobutyronitrile (AIBN) or benzoyl peroxide is usually employed to initiate this reaction. When bromination is complete, the cooled reaction mixture is filtered to remove the by-product succinimide and the filtrate is concentrated in vacuo. The benzylic type bromides of Formula IXa are often obtained in a sufficiently pure condition for further transformations. If not, they can be purified by vacuum distillation or column chromatography.

Benzylic type chlorides of Formula IXb (L=chlorine) may be most efficiently synthesized by one of two methods, both of which are well known in the chemical literature. First, benzylic type chlorides, IXb, can be prepared from the appropriate methyl imidazole or pyrazole type derivatives of Formula XII by reaction with N-chlorosuccinimide (NCS). This reaction is depicted below in Equation 11.

Equation 11

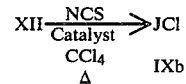

The reaction of Equation 11 can be carried out in a manner analogous to that described for the NBS bromination in Equation 10.

In compounds of Formula XII where J is J-1, J-2 or J-3, ring halogenation may occur together with benzylic-type halogenation in Equations 10 and 11. Subsequent removal of the ring halogen after conversion to the desired sulfonamide IV may be carried out by methods known in the art.

Alternatively, benzylic type chlorides of Formula IXb may be prepared from the appropriate benzylic type alcohols of Formula XIII as shown below in Equation 12.

Equation 12

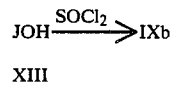

There exists a variety of well known methods for converting alkyl alcohols to the corresponding chlorides. One of the most common procedures involves reaction of the alcohol with thionyl chloride either alone or in the presence of a trace of a suitable base such as pyridine. For relevant examples, see the following references: H. Gilman and J. E. Kirby, *J. Am. Chem. Soc.*, 51, 3475 (1929); H. Gilman and A. P. Hewlett, *Rec. Trav. Chim.*, 51, 93 (1932); and M. S. Newman, *J. Am. Chem. Soc.*, 62, 2295 (1940).

The requisite heterocyclic methanols of Formula XIII may be prepared by reduction of an appropriately substituted imidazole, pyrazole, pyridinyl or thienyl carboxylic acid. The reduction is best effected by treatment of an appropriately substituted imidazole or pyrazole carboxylic acid with a suitable reducing agent such as diborane in tetrahydrofuran solvent. For a description of this procedure, refer to H. C. Brown, *J. Org. Chem.*, 38, 2786 (1973).

Substituted heterocyclic carboxylic acid derivatives, the functionalized heterocyclic methanols of Formula XIII and heterocyclic methyl compounds of Formula XII can be prepared by any of several possible synthetic routes known to one skilled in the art.

The heterocyclic amines of Formula III can be prepared by methods known in the literature or simple modifications thereof, by those skilled in the art. For instance, EP-A No. 84,224 (published July 27, 1983) and W. Braker et al, *J. Am. Chem. Soc.* 1947, 69, 3072 describe methods for preparing aminopyrimidines and triazines substituted by acetal groups. Also, South African Patent Application Nos. 825,045 and 825,671 describe methods for preparing aminopyrimidines and triazines substituted by haloalkyl or haloalkylthio groups such as $OCH_2CH_2F$, $OCH_2CF_3$, $SCF_2H$, and $OCF_2H$ among other groups. South African Patent Application No. 837,434 (published Oct. 5, 1983) describes methods for the synthesis of cyclopropylpyrimidines and triazines substituted by such groups as alkyl, haloalkyl, alkoxy, haloalkoxy, alkylamino, dialkylamino, and alkoxyalkyl.

The 5,6-dihydrofuro[2.3-d]pyrimidin-2-amines, and the cyclopenta[d]pyrimidin-2-amines, of formula III, where A is A-2, and the 6,7-dihydro-5H-pyrano[2.3-d]pyrimidin-2-amines, of formula III, where A is A-3, can be prepared as described in EP-A No. 15,863. The furo[2.3-d]-pyrimidin-2-amines, of formula III, where A is A-4, are described in EP-A No. 46,677. Heterocycles of formula III, where A is A-5, may be prepared as described in EP-A No. 73,562. Heterocycles of Formula III, where A is A-6, may be prepared by methods taught in EP-A No. 94,260.

In addition, general methods for preparing aminopyrimidines and triazines have been reviewed in the following publications.

- "The Chemistry of Heterocyclic Compounds", a series published by Interscience Publishers, Inc., New York and London;
- "Pyrimidines", Vol. 16 of the same series by D. J. Brown;
- "s-Triazines and Derivatives", Vol. 13 of the same series by E. M. Smolin and L. Rappaport; and
- F. C. Schaefer, U.S. Pat. No. 3,154,547 and K. R. Huffman and F. C. Schaefer, *J. Org. Chem.*, 28, 1812 (1963), which describe the synethsis of triazines.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation for another. Cationic exchange can be effected by direct contacting of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is illustrated by the following examples.

EXAMPLE 1

Ethyl 5-(chloromethyl)-1,3-dimethyl-1H-pyrazole-4-carboxylate

To 5.3 g (26.8 mmol) of 4-ethoxycarbonyl-5-(1-hydroxymethyl)-1,3-dimethylpyrazole prepared by the method of S. Gelin, et al., *J. Heterocyclic Chem.*, 16, (1979) 1117-20, was added 1.95 ml (26.8 mmol) of thionyl chloride, dropwise. Gas evolution and an exotherm occurred. The solution was cooled with an ice bath. After ten minutes the solution gave a solid, m.p. 81°–83° C., $^1$H NMR (90 MHz, CDCl$_3$): δ 1.4 (t, OCCH$_3$, 3H); 2.65 (s, CH$_3$, 3H); 4.2 (s, NCH$_3$, 3H); 4.4 (q, OCH$_2$C, 2H); 5.2 (s, CH$_2$Cl, 2H).

This material was combined with the product of a second reaction (5.0 g of 4-ethoxycarbonyl-5-(1-hydroxymethyl)-1,3-dimethylpyrazole and 1.93 ml thionyl chloride), dissolved in dichloromethane, washed with brine, dried (MgSO$_4$) and concentrated to give 10.7 g of a solid, mp. 81°–83° C.

EXAMPLE 2

Ethyl 5-[[(amino)(imino)methyl]thiomethyl]-1,3-dimethyl-1H-pyrazole-4-carboxylate A solution under nitrogen was prepared from 10.7 g of the compound produced in Example 1 and 3.95 g of thiourea in 200 ml of ethanol. After refluxing the solution four hours, it was allowed to stir at room temperature overnight. The solvent was removed under reduced pressure. Then, the residue was triturated with hexane to give 16 g of solid (wet weight), m.p. 175°–180° C.

EXAMPLE 3

Ethyl 5-methanesulfonamide-1,3-dimethyl-1H-pyrazole-4-carboxylate

To 14 g of the compound produced in Example 2, dissolved in 90 ml of water at 5° C. was added 10 ml of chlorine dropwise. The rate of addition was monitored so that the temperature did not exceed 20° C. A precipitate formed. The aqueous portion was decanted off and the residue was dissolved in dichloromethane, washed with a saturated sodium bicarbonate solution, dried (MgSO$_4$) and concentrated. The residue was dissolved in 100 ml of THF. To a 75 ml portion of the THF solution, cooled to 5° C., was added 1.5 ml of concentrated ammonium hydroxide solution in 10 ml of THF. A suspension formed, which was stirred for six hours. The reaction mixture was filtered and the mother liquor was concentrated under reduced pressure. The residue, triturated with ethyl acetate-diethyl ether (40:60) gave 3.0 g of a light yellow solid, m.p. 135°–138° C.; $^1$H NMR (90 MHz, d$_6$-DMSO): δ 1.2 (t, CH$_3$, 3H); 2.3 (s, CH$_3$, 3H); 3.8 (s, NCH$_3$, 3H); 4.2 (q, OCH$_2$, 2H); 4.8 (s, CH$_2$SO$_2$, 2H); 7.1 (bs, NH$_2$, 2H).

EXAMPLE 4

Ethyl 5-[[[[4,6-dimethoxypyrimidin-2-yl]aminocarbonyl]aminosulfonyl]methyl]-1,3-dimethyl-1H-pyrazole-4-carboxylate In a dry flask under nitrogen was stirred 0.33 g of the sulfonamide from Example 3 and 0.35 g of phenyl (4,6-dimethoxypyrimidin-2-yl)carbamate and 30 ml of dry acetonitrile. Then 0.19 ml of 1,8-diazabicyclo[5.4.0]undec-7-ene was added via syringe and the solution stirred overnight. Then 50 ml of water was added, followed by a dropwise addition of 1 NHCl until a precipitate formed. The suspension was filtered. The filtrant, after being triturated with diethyl ether, gave 0.4 g of solid, m.p. 190° C.; 1R (Nujol) 1711 and 1680 (C═O) cm$^{-1}$; $^1$H NMR (200 MHz, CDCl$_3$): δ 1.25 (t, CH$_3$, 3H); 2.38 (s, CH$_3$, 3H); 3.80 (s, OCH$_3$, 6H); 3.94 (s, NCH$_3$, 3H);

4.15 (q, OCH$_2$, 2H); 5.23 (s, CH$_2$SO$_2$, 2H); 5.71 (s, bs, CH, 1H); 7.35 (bs, NH, 1H) and 12.4 (bs, NH, 1H).

The invention is further exemplified, but not limited to, the compounds in Tables I-XXII. The compounds depicted in these tables may be prepared by methods described in Examples 1-4, or by modifications thereof apparent to those skilled in the art.

TABLE I

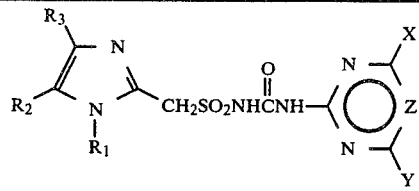

| R$_1$ | R$_2$ | R$_3$ | X | Y | Z | m.p. (°C.) |
|---|---|---|---|---|---|---|
| H | H | H | CH$_3$ | CH$_3$ | CH | |
| H | H | H | CH$_3$ | OCH$_3$ | CH | |
| CH$_3$ | H | H | OCH$_3$ | OCH$_3$ | CH | |
| CH$_3$ | H | H | CH$_3$ | CH$_3$ | N | |
| CH$_3$ | H | H | CH$_3$ | OCH$_3$ | N | |
| CH$_2$CH$_3$ | H | H | OCH$_3$ | OCH$_3$ | N | |
| CH$_2$CH$_2$CH$_3$ | H | H | CH$_3$ | OCH$_2$CH$_3$ | CH | |
| CH$_2$CH$_2$CH$_3$ | H | H | CH$_3$ | OCH$_3$ | CH | |
| CH$_2$CH$_2$CH$_3$ | H | H | OCH$_3$ | OCH$_3$ | CH | |
| CH$_2$CH$_2$CH$_3$ | H | H | CH$_3$ | CH$_3$ | N | |
| CH(CH$_3$)$_2$ | H | H | CH$_3$ | OCH$_3$ | N | |
| CO$_2$CH$_3$ | H | H | OCH$_3$ | OCH$_3$ | N | |
| CO$_2$CH$_3$ | H | H | Br | OCH$_3$ | CH | |
| CO$_2$CH$_3$ | H | H | CH$_3$ | OCH$_3$ | CH | |
| CO$_2$CH$_3$ | H | H | OCH$_3$ | OCH$_3$ | CH | |
| CO$_2$CH$_3$ | H | H | CH$_3$ | CH$_3$ | N | |
| CO$_2$CH$_3$ | H | H | CH$_3$ | OCH$_3$ | N | |
| CO$_2$CH$_2$CH$_3$ | H | H | OCH$_3$ | OCH$_3$ | N | |
| C(O)N(CH$_3$)$_2$ | H | H | OCH$_3$ | CH$_2$OCH$_3$ | CH | |
| CO$_2$CH$_2$CH$_3$ | H | H | CH$_3$ | OCH$_3$ | CH | |
| SO$_2$N(CH$_3$)$_2$ | H | H | OCH$_3$ | OCH$_3$ | CH | |
| SO$_2$N(CH$_3$)CH$_2$CH$_3$ | H | H | CH$_3$ | CH$_3$ | N | |
| SO$_2$N(CH$_2$CH$_3$)$_2$ | H | H | CH$_3$ | OCH$_3$ | N | |
| SO$_2$CH$_3$ | H | H | OCH$_3$ | OCH$_3$ | N | |
| SO$_2$CH$_3$ | H | H | CH$_3$ | CH$_2$F | CH | |
| SO$_2$CH$_3$ | H | H | CH$_3$ | OCH$_3$ | CH | |
| SO$_2$CH$_3$ | H | H | OCH$_3$ | OCH$_3$ | CH | |
| SO$_2$CH$_3$ | H | H | Cl | OCH$_3$ | CH | |
| SO$_2$CH$_2$CH$_3$ | H | H | OCH$_3$ | OCH$_3$ | CH | |
| H | CH$_3$ | H | CH$_3$ | CH$_3$ | CH | |
| H | CH$_3$ | H | CH$_3$ | OCH$_3$ | CH | |
| CH$_3$ | CH$_3$ | H | OCH$_3$ | OCH$_3$ | CH | |
| CH$_3$ | CH$_3$ | H | CH$_3$ | CH$_3$ | N | |
| CH$_3$ | CH$_3$ | H | CH$_3$ | OCH$_3$ | N | |
| CH$_2$CH$_3$ | CH$_3$ | H | OCH$_3$ | OCH$_3$ | N | |
| CH$_2$CH$_2$CH$_3$ | CH$_3$ | H | CH$_3$ | OCH$_2$CH$_3$ | CH | |
| CH$_2$CH$_2$CH$_3$ | CH$_3$ | H | CH$_3$ | OCH$_3$ | CH | |
| CH$_2$CH$_2$CH$_3$ | CH$_3$ | H | OCH$_3$ | OCH$_3$ | CH | |
| CH$_2$CH$_2$CH$_3$ | CH$_3$ | H | CH$_3$ | CH$_3$ | N | |
| CH(CH$_3$)$_2$ | CH$_3$ | H | CH$_3$ | OCH$_3$ | N | |
| CO$_2$CH$_3$ | CH$_3$ | H | OCH$_3$ | OCH$_3$ | N | |
| CO$_2$CH$_3$ | CH$_3$ | H | OCH$_2$CF$_3$ | CH$_3$ | CH | |
| CO$_2$CH$_3$ | CH$_3$ | H | CH$_3$ | OCH$_3$ | CH | |
| CO$_2$CH$_3$ | CH$_3$ | H | OCH$_3$ | OCH$_3$ | CH | |
| C(O)N(H)C$_2$H$_5$ | CH$_3$ | H | CH$_3$ | CH$_3$ | N | |
| CO$_2$CH$_3$ | CH$_3$ | H | CH$_3$ | OCH$_3$ | N | |
| CO$_2$CH$_2$CH$_3$ | CH$_3$ | H | OCH$_3$ | OCH$_3$ | N | |
| CO$_2$CH$_2$CH$_3$ | CH$_3$ | H | OCH$_3$ | CH$_2$OCH$_3$ | CH | |
| CO$_2$CH$_2$CH$_3$ | CH$_3$ | H | CH$_3$ | OCH$_3$ | CH | |
| SO$_2$N(CH$_3$)$_2$ | CH$_3$ | H | OCH$_3$ | OCH$_3$ | CH | |
| SO$_2$N(CH$_3$)CH$_2$CH$_3$ | CH$_3$ | H | CH$_3$ | CH$_3$ | N | |
| SO$_2$N(CH$_2$CH$_3$)$_2$ | CH$_3$ | H | CH$_3$ | OCH$_3$ | N | |
| SO$_2$CH$_3$ | CH$_3$ | H | OCH$_3$ | OCH$_3$ | N | |
| SO$_2$CH$_3$ | CH$_3$ | H | CH$_3$ | CH$_3$ | CH | |
| SO$_2$CH$_3$ | CH$_3$ | H | CH$_3$ | OCH$_3$ | CH | |
| SO$_2$CH$_3$ | CH$_3$ | H | OCH$_3$ | OCH$_3$ | CH | |
| SO$_2$CH$_3$ | CH$_3$ | H | Cl | OCH$_3$ | CH | |
| SO$_2$CH$_2$CH$_3$ | CH$_3$ | H | OCH$_3$ | OCH$_3$ | CH | |
| H | H | CH$_3$ | CH$_3$ | CH$_3$ | CH | |
| H | H | CH$_3$ | CH$_3$ | OCH$_3$ | CH | |
| CH$_3$ | H | CH$_3$ | OCH$_3$ | OCH$_3$ | CH | |
| CH$_3$ | H | CH$_3$ | CH$_3$ | CH$_3$ | N | |
| CH$_3$ | H | CH$_3$ | CH$_3$ | OCH$_3$ | N | |
| CH$_2$CH$_3$ | H | CH$_3$ | OCH$_3$ | Δ | N | |
| CH$_2$CH$_2$CH$_3$ | H | CH$_3$ | CH$_3$ | OCH$_2$CH$_3$ | CH | |
| CH$_2$CH$_2$CH$_3$ | H | CH$_3$ | CH$_3$ | OCH$_3$ | CH | |
| CH$_2$CH$_2$CH$_3$ | H | CH$_3$ | OCH$_3$ | OCH$_3$ | CH | |

TABLE I-continued

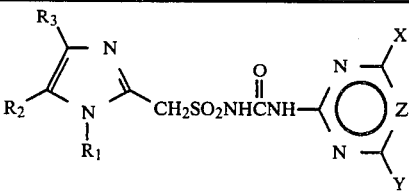

| $R_1$ | $R_2$ | $R_3$ | X | Y | Z | m.p. (°C.) |
|---|---|---|---|---|---|---|
| $CH_2CH_2CH_3$ | H | $CH_3$ | $CH_3$ | $CH_3$ | N | |
| $CH(CH_3)_2$ | H | $CH_3$ | $CH_3$ | $OCH_3$ | N | |
| $C(O)NH_2$ | H | $CH_3$ | $OCH_3$ | $N(CH_3)_2$ | N | |
| $CO_2CH_3$ | H | $CH_3$ | $CH_3$ | $CH_3$ | CH | |
| $CO_2CH_3$ | H | $CH_3$ | $CH_3$ | $OCH_3$ | CH | |
| $CO_2CH_3$ | H | $CH_3$ | $OCH_3$ | $OCH_3$ | CH | |
| $CO_2CH_3$ | H | $CH_3$ | $CH_3$ | $CH_3$ | N | |
| $CO_2CH_3$ | H | $CH_3$ | $CH_3$ | $OCH_3$ | N | |
| $CO_2CH_2CH_3$ | H | $CH_3$ | $OCH_3$ | $OCH_3$ | N | |
| $CO_2CH_2CH_3$ | H | $CH_3$ | $OCH_3$ | $CH_2OCH_3$ | CH | |
| $CO_2CH_2CH_3$ | H | $CH_3$ | $CH_3$ | $OCH_3$ | CH | |
| $SO_2N(CH_3)_2$ | H | $CH_3$ | $OCH_3$ | $OCH_3$ | CH | |
| $SO_2N(CH_3)CH_2CH_3$ | H | $CH_3$ | $CH_3$ | $CH_3$ | N | |
| $SO_2N(CH_2CH_3)_2$ | H | $CH_3$ | $CH_3$ | $OCH_2CH_2F$ | N | |
| $SO_2CH_3$ | H | $CH_3$ | $OCH_3$ | $OCH_3$ | N | |
| $SO_2CH_3$ | H | $CH_3$ | $OCHF_2$ | $CH_3$ | CH | |
| $SO_2CH_3$ | H | $CH_3$ | $CH_3$ | $OCH_3$ | CH | |
| $SO_2CH_3$ | H | $CH_3$ | $OCH_3$ | $OCH_3$ | CH | |
| $SO_2CH_3$ | H | $CH_3$ | Cl | $OCH_3$ | CH | |
| $SO_2CH_2CH_3$ | H | $CH_3$ | $OCH_3$ | $OCH_3$ | CH | |
| H | $CH_3$ | $CH_3$ | $CH_3$ | $CF_3$ | CH | |
| H | $CH_3$ | $CH_3$ | $CH_3$ | $OCH_3$ | CH | |
| $CH_3$ | $CH_3$ | $CH_3$ | $OCH_3$ | $OCH_3$ | CH | |
| $CH_3$ | $CH_3$ | $CH_3$ | $CH_3$ | $SCH_3$ | N | |
| $CH_3$ | $CH_3$ | $CH_3$ | $CH_3$ | $OCH_3$ | N | |
| $CH_2CH_3$ | $CH_3$ | $CH_3$ | $OCH_3$ | $OCH_3$ | N | |
| $CH_2CH_2CH_3$ | $CH_3$ | $CH_3$ | $CH_3$ | $OCH_2CH_3$ | CH | |
| $CH_2CH_2CH_3$ | $CH_3$ | $CH_3$ | $CH_3$ | $OCH_3$ | CH | |
| $CH_2CH_2CH_3$ | $CH_3$ | $CH_3$ | $OCH_3$ | $OCH_2C\equiv CH$ | CH | |
| $CH_2CH_2CH_3$ | $CH_3$ | $CH_3$ | $CH_3$ | $CH_3$ | N | |
| $CH(CH_3)_2$ | $CH_3$ | $CH_3$ | $CH_3$ | $OCH_3$ | N | |
| $CO_2CH_3$ | $CH_3$ | $CH_3$ | $OCH_3$ | $OCH_3$ | N | |
| $CO_2CH_3$ | $CH_3$ | $CH_3$ | $CH_3$ | $OCH_2CH_3OCH_3$ | CH | |
| $CO_2CH_3$ | $CH_3$ | $CH_3$ | $OCH_3$ | $OCH_3$ | CH | |
| $CO_2CH_3$ | $CH_3$ | $CH_3$ | $CH_3$ | $CH_3$ | N | |
| $CO_2CH_3$ | $CH_3$ | $CH_3$ | $CH_3$ | $OCH_3$ | N | |
| $C(O)N(C_2H_5)_2$ | $CH_3$ | $CH_3$ | $OCH_3$ | $OCH_3$ | N | |
| $CO_2CH_2CH_3$ | $CH_3$ | $CH_3$ | $OCH_3$ | $CH_2OCH_3$ | CH | |
| $CO_2CH_2CH_3$ | $CH_3$ | $CH_3$ | $CH_3$ | $OCH_3$ | CH | |
| $SO_2N(CH_3)_2$ | $CH_3$ | $CH_3$ | $OCH_3$ | $CH(OCH_3)_2$ | CH | |
| $SO_2N(CH_3)CH_2CH_3$ | $CH_3$ | $CH_3$ | $CH_3$ | $CH_3$ | N | |
| $SO_2N(CH_2CH_3)_2$ | $CH_3$ | $CH_3$ | $CH_3$ | $OCH_3$ | N | |
| $SO_2CH_3$ | $CH_3$ | $CH_3$ | $OCH_3$ | $OCH_3$ | N | |
| $SO_2CH_3$ | $CH_3$ | $CH_3$ | $CH_3$ | $CH_3$ | CH | |
| $SO_2CH_3$ | $CH_3$ | $CH_3$ | $CH_3$ | $OCH_3$ | CH | |
| $SO_2CH_3$ | $CH_3$ | $CH_3$ | $OCH_3$ | $OCH_3$ | CH | |
| $SO_2CH_3$ | $CH_3$ | $CH_3$ | Cl | $OCH_3$ | CH | |
| $SO_2CH_2CH_3$ | $CH_3$ | $CH_3$ | $OCH_3$ | 1,3-dioxolan-2-yl | CH | |

TABLE II

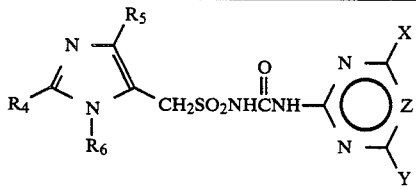

| $R_4$ | $R_5$ | $R_6$ | X | Y | Z | m.p. (°C.) |
|---|---|---|---|---|---|---|
| H | $CH_3$ | H | $CH_3$ | $OCH_3$ | CH | |
| H | $CH_3$ | H | $OCH_3$ | $OCH_3$ | CH | |
| H | $CO_2CH_3$ | H | $CH_3$ | $CH_3$ | N | |
| H | $CO_2CH_3$ | H | $CH_3$ | $OCH_3$ | N | |
| H | $CO_2CH_3$ | H | $OCH_3$ | $OCH_3$ | N | |
| H | $CO_2CH_3$ | H | $CH_3$ | $OCF_2H$ | CH | |
| H | $CO_2CH_3$ | H | $CH_3$ | $OCH_3$ | CH | |

TABLE II-continued

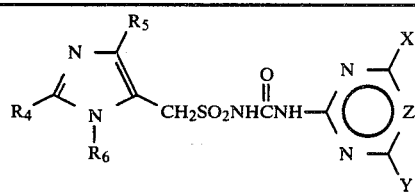

| R4 | R5 | R6 | X | Y | Z | m.p. (°C.) |
|---|---|---|---|---|---|---|
| H | CO2CH3 | H | OCH3 | OCH3 | CH | |
| H | CO2CH2CH3 | H | CH3 | CH3 | N | |
| H | CO2CH2CH3 | H | CH3 | OCH2CH3 | N | |
| H | SO2N(CH3)2 | H | OCH3 | NHCH3 | N | |
| H | SO2N(CH3)2 | H | CH3 | CH3 | CH | |
| H | SO2N(CH3)2 | H | CH3 | C≡CH | CH | |
| H | SO2N(CH3)2 | H | OCH3 | OCH3 | CH | |
| H | SO2N(CH3)2 | H | CH3 | CH3 | N | |
| H | SO2N(CH3)2 | H | CH3 | OCH3 | N | |
| H | SO2N(CH3)CH2CH3 | H | OCH3 | OCH3 | N | |
| H | SO2N(OCH3)CH3 | H | CH3 | CH3 | CH | |
| H | SO2N(CH2CH3)2 | H | CH3 | OCH3 | CH | |
| H | SO2N(CH2CH3)2 | H | Br | OCH3 | CH | |
| H | SO2CH3 | H | CH3 | CH3 | N | |
| H | SO2CH3 | H | CH3 | OCH3 | N | |
| H | Cl | H | OCH3 | OCH3 | N | |
| H | SO2CH3 | H | CH3 | CH2CH3 | CH | |
| H | SO2CH3 | H | CH3 | OCH3 | CH | |
| H | SO2CH3 | H | OCH3 | CH(OCH3)2 | CH | |
| H | SO2CH2CH3 | H | Cl | OCH3 | CH | |
| H | SO2CH2CH3 | H | OCH3 | OCH3 | N | |
| H | H | CH3 | CH3 | CH3 | CH | |
| H | CH3 | CH3 | CH3 | OCH3 | CH | |
| H | CH3 | CH3 | OCH3 | OCH3 | CH | |
| H | CO2CH3 | CH3 | CH3 | CH3 | N | |
| H | CO2CH3 | CH3 | CH3 | OCH3 | N | |
| H | CO2CH3 | CH3 | OCH3 | OCH3 | N | |
| H | CO2CH3 | CH3 | CH3 | CH3 | CH | |
| H | CO2CH3 | CH3 | CH3 | OCH3 | CH | |
| H | CO2CH3 | CH3 | OCH3 | OCH3 | CH | |
| H | CO2CH2CH3 | CH3 | CH3 | CH3 | N | |
| H | CO2CH2CH3 | CH3 | CH3 | OCH2CH3 | N | |
| H | SO2N(CH3)2 | CH3 | OCH3 | OCH3 | N | |
| H | SO2N(CH3)2 | CH3 | CH3 | CH3 | CH | |
| H | SO2N(CH3)2 | CH3 | CH3 | OCH3 | CH | |
| H | SO2N(CH3)2 | CH3 | OCH3 | OCH3 | CH | |
| H | SO2N(CH3)2 | CH3 | CH3 | CH3 | N | |
| H | SO2N(CH3)2 | CH3 | CH3 | OCH3 | N | |
| H | SO2N(CH3)CH2CH3 | CH3 | OCH3 | OCH3 | N | |
| H | SO2N(OCH3)CH3 | CH3 | CH3 | CH3 | CH | |
| H | SO2N(CH2CH3)2 | CH3 | CH3 | OCH2CH=CH2 | CH | |
| H | SO2N(CH2CH3)2 | CH3 | OCH3 | OCH3 | CH | |
| H | SO2CH3 | CH3 | CH3 | CH3 | N | |
| H | SO2CH3 | CH3 | CH3 | OCH3 | N | |
| H | SO2CH3 | CH3 | OCH3 | OCH3 | N | |
| H | SO2CH3 | CH3 | CH3 | CH2CH3 | CH | |
| H | Br | CH3 | CH3 | OCH3 | CH | |
| H | SO2CH3 | CH3 | OCH3 | OCH3 | CH | |
| H | SO2CH2CH3 | CH3 | Cl | OCH3 | CH | |
| H | SO2CH2CH3 | CH3 | OCH3 | OCH3 | N | |
| H | H | CH2CH2CH3 | CH3 | CH3 | CH | |
| H | CH3 | CH2CH2CH3 | CH3 | OCH3 | CH | |
| H | CH3 | CH2CH2CH3 | OCH3 | OCH3 | CH | |
| H | CO2CH3 | CH2CH2CH3 | CH3 | CH3 | N | |
| H | CO2CH3 | CH2CH2CH3 | CH3 | OCH3 | N | |
| H | CO2CH3 | CH2CH2CH3 | OCH3 | OCH3 | N | |
| H | CO2CH3 | CH2CH2CH3 | CH3 | CH3 | CH | |
| H | CO2CH3 | CH2CH2CH3 | CH3 | OCH3 | CH | |
| H | CO2CH3 | CH2CH2CH3 | OCH3 | SCH3 | CH | |
| H | CO2CH2CH3 | CH2CH2CH3 | CH3 | CH3 | N | |
| H | CO2CH2CH3 | CH2CH2CH3 | CH3 | OCH2CH3 | N | |
| H | SO2N(CH3)2 | CH2CH2CH3 | OCH2CF3 | OCH3 | N | |
| H | SO2N(CH3)2 | CH2CH2CH3 | CH3 | CH3 | CH | |
| H | SO2N(CH3)2 | CH2CH2CH3 | CH3 | OCH3 | CH | |
| H | SO2N(CH3)2 | CH2CH2CH3 | OCH3 | OCH3 | CH | |
| H | SO2N(CH3)2 | CH2CH2CH3 | CH3 | CH3 | N | |
| H | SO2N(CH3)2 | CH2CH2CH3 | CH3 | OCH3 | N | |
| H | SO2N(CH3)CH2CH3 | CH2CH2CH3 | OCH3 | OCH3 | N | |
| H | SO2N(OCH3)CH3 | CH2CH2CH3 | CH3 | CH3 | CH | |
| H | SO2N(CH2CH3)2 | CH2CH2CH3 | CH3 | OCH3 | CH | |
| H | SO2N(CH2CH3)2 | CH2CH2CH3 | OCH3 | OCH3 | CH | |

TABLE II-continued

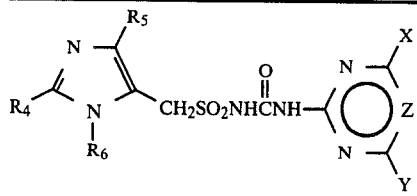

| R$_4$ | R$_5$ | R$_6$ | X | Y | Z | m.p. (°C.) |
|---|---|---|---|---|---|---|
| H | SO$_2$CH$_3$ | CH$_2$CH$_2$CH$_3$ | CH$_3$ | CH$_3$ | N | |
| H | SO$_2$CH$_3$ | CH$_2$CH$_2$CH$_3$ | CH$_3$ | OCH$_3$ | N | |
| H | SO$_2$CH$_3$ | CH$_2$CH$_2$CH$_3$ | OCH$_3$ | OCH$_3$ | N | |
| H | SO$_2$CH$_3$ | CH$_2$CH$_2$CH$_3$ | CH$_3$ | CH$_2$CH$_3$ | CH | |
| H | SO$_2$CH$_3$ | CH$_2$CH$_2$CH$_3$ | CH$_3$ | OCH$_3$ | CH | |
| H | SO$_2$CH$_3$ | CH$_2$CH$_2$CH$_3$ | OCH$_3$ | OCH$_3$ | CH | |
| H | SO$_2$CH$_2$CH$_3$ | CH$_2$CH$_2$CH$_3$ | Cl | CH$_2$F | CH | |
| H | SO$_2$CH$_2$CH$_3$ | CH$_2$CH$_2$CH$_3$ | OCH$_3$ | OCH$_3$ | N | |
| CH$_3$ | H | CH$_3$ | CH$_3$ | CH$_3$ | CH | |
| CH$_3$ | CH$_3$ | CH$_3$ | CH$_3$ | OCH$_3$ | CH | |
| CH$_3$ | CH$_3$ | CH$_3$ | OCH$_3$ | OCH$_3$ | CH | |
| CH$_3$ | CO$_2$CH$_3$ | CH$_3$ | CH$_3$ | CH$_3$ | N | |
| CH$_3$ | CO$_2$CH$_3$ | CH$_3$ | CH$_3$ | OCH$_3$ | N | |
| CH$_3$ | CO$_2$CH$_3$ | CH$_3$ | OCH$_3$ | OCH$_3$ | N | |
| CH$_3$ | CO$_2$CH$_3$ | CH$_3$ | CH$_3$ | CH$_3$ | CH | |
| CH$_3$ | CO$_2$CH$_3$ | CH$_3$ | CH$_3$ | OCH$_3$ | CH | |
| CH$_3$ | CO$_2$CH$_3$ | CH$_3$ | OCH$_3$ | NH$_2$ | CH | |
| CH$_3$ | CO$_2$CH$_2$CH$_3$ | CH$_3$ | CH$_3$ | CH$_3$ | N | |
| CH$_3$ | CO$_2$CH$_2$CH$_3$ | CH$_3$ | CH$_3$ | OCH$_2$CH$_3$ | N | |
| CH$_3$ | SO$_2$N(CH$_3$)$_2$ | CH$_3$ | OCH$_3$ | OCH$_3$ | N | |
| CH$_3$ | SO$_2$N(CH$_3$)$_2$ | CH$_3$ | CH$_3$ | CH$_3$ | CH | |
| CH$_3$ | SO$_2$N(CH$_3$)$_2$ | CH$_3$ | CH$_3$ | OCH$_3$ | CH | |
| CH$_3$ | SO$_2$N(CH$_3$)$_2$ | CH$_3$ | OCH$_3$ | OCH$_3$ | CH | |
| CH$_3$ | SO$_2$N(CH$_3$)$_2$ | CH$_3$ | CH$_3$ | CH$_3$ | N | |
| CH$_3$ | Br | CH$_3$ | CH$_3$ | OCH$_3$ | N | |
| CH$_3$ | SO$_2$N(CH$_3$)CH$_2$CH$_3$ | CH$_3$ | OCH$_3$ | OCH$_3$ | N | |
| CH$_3$ | SO$_2$N(OCH$_3$)CH$_3$ | CH$_3$ | CH$_3$ | CH$_3$ | CH | |
| CH$_3$ | SO$_2$N(CH$_2$CH$_3$)$_2$ | CH$_3$ | CH$_3$ | OCH$_3$ | CH | |
| CH$_3$ | SO$_2$N(CH$_2$CH$_3$)$_2$ | CH$_3$ | OCH$_3$ | OCH$_3$ | CH | |
| CH$_3$ | SO$_2$CH$_3$ | CH$_3$ | CH$_3$ | CH$_3$ | N | |
| CH$_3$ | SO$_2$CH$_3$ | CH$_3$ | CH$_3$ | OCH$_3$ | N | |
| CH$_3$ | SO$_2$CH$_3$ | CH$_3$ | OCH$_3$ | OCH$_3$ | N | |
| CH$_3$ | SO$_2$CH$_3$ | CH$_3$ | CH$_3$ | CH$_2$CH$_3$ | CH | |
| CH$_3$ | SO$_2$CH$_3$ | CH$_3$ | CH$_3$ | OCH$_3$ | CH | |
| CH$_3$ | SO$_2$CH$_3$ | CH$_3$ | OCF$_2$H | CH$_3$ | CH | |
| CH$_3$ | SO$_2$CH$_2$CH$_3$ | CH$_3$ | Cl | OCH$_3$ | CH | |
| CH$_3$ | SO$_2$CH$_2$CH$_3$ | CH$_3$ | OCH$_3$ | OCH$_3$ | N | |
| CH$_3$ | H | CH$_2$CH$_2$CH$_3$ | CH$_3$ | CH$_3$ | CH | |
| CH$_3$ | CH$_3$ | CH$_2$CH$_2$CH$_3$ | CH$_3$ | OCH$_3$ | CH | |
| CH$_3$ | CH$_3$ | CH$_2$CH$_2$CH$_3$ | OCH$_3$ | OCH$_3$ | CH | |
| CH$_3$ | CO$_2$CH$_3$ | CH$_2$CH$_2$CH$_3$ | CH$_3$ | CH$_3$ | N | |
| CH$_3$ | CO$_2$CH$_3$ | CH$_2$CH$_2$CH$_3$ | CH$_3$ | OCH$_3$ | N | |
| CH$_3$ | CO$_2$CH$_3$ | CH$_2$CH$_2$CH$_3$ | OCH$_3$ | OCH$_3$ | N | |
| CH$_3$ | CO$_2$CH$_3$ | CH$_2$CH$_2$CH$_3$ | CH$_3$ | CH$_3$ | CH | |
| CH$_3$ | CO$_2$CH$_3$ | CH$_2$CH$_2$CH$_3$ | CH$_3$ | OCH$_3$ | CH | |
| CH$_3$ | CO$_2$CH$_3$ | CH$_2$CH$_2$CH$_3$ | OCH$_3$ | OCH$_3$ | CH | |
| CH$_3$ | CO$_2$CH$_2$CH$_3$ | CH$_2$CH$_2$CH$_3$ | CH$_3$ | CH$_3$ | N | |
| CH$_3$ | CO$_2$CH$_2$CH$_3$ | CH$_2$CH$_2$CH$_3$ | CH$_3$ | OCH$_2$CH$_3$ | N | |
| CH$_3$ | SO$_2$N(CH$_3$)$_2$ | CH(CH$_3$)$_2$ | OCH$_3$ | OCH$_3$ | N | |
| CH$_3$ | SO$_2$N(CH$_3$)$_2$ | CH$_2$CH$_2$CH$_3$ | CH$_3$ | CH$_3$ | CH | |
| CH$_3$ | SO$_2$N(CH$_3$)$_2$ | CH$_2$CH$_2$CH$_3$ | CH$_3$ | OCH$_3$ | CH | |
| CH$_3$ | SO$_2$N(CH$_3$)$_2$ | CH$_2$CH$_2$CH$_3$ | OCH$_3$ | OCH$_3$ | CH | |
| CH$_3$ | SO$_2$N(CH$_3$)$_2$ | CH$_2$CH$_2$CH$_3$ | CH$_3$ | CH$_3$ | N | |
| CH$_3$ | SO$_2$N(CH$_3$)$_2$ | CH$_2$CH$_2$CH$_3$ | CH$_3$ | OCH$_3$ | N | |
| CH$_3$ | SO$_2$N(CH$_3$)CH$_2$CH$_3$ | CH$_2$CH$_2$CH$_3$ | OCH$_3$ | OCH$_3$ | N | |
| CH$_3$ | SO$_2$N(OCH$_3$)CH$_3$ | CH$_2$CH$_2$CH$_3$ | CH$_3$ | CH$_3$ | CH | |
| CH$_3$ | SO$_2$N(CH$_2$CH$_3$)$_2$ | CH$_2$CH$_2$CH$_3$ | CH$_3$ | OCH$_3$ | CH | |
| CH$_3$ | SO$_2$N(CH$_2$CH$_3$)$_2$ | CH$_2$CH$_2$CH$_3$ | OCH$_3$ | OCH$_3$ | CH | |
| CH$_3$ | SO$_2$CH$_3$ | CH$_2$CH$_2$CH$_3$ | CH$_3$ | CH$_3$ | N | |
| CH$_3$ | SO$_2$CH$_3$ | CH$_2$CH$_2$CH$_3$ | CH$_3$ | OCH$_3$ | N | |
| CH$_3$ | SO$_2$CH$_3$ | CH$_2$CH$_2$CH$_3$ | OCH$_3$ | OCH$_3$ | N | |
| CH$_3$ | SO$_2$CH$_3$ | CH$_2$CH$_2$CH$_3$ | CH$_3$ | CH$_2$CH$_3$ | CH | |
| CH$_3$ | SO$_2$CH$_3$ | CH$_2$CH$_2$CH$_3$ | CH$_3$ | OCH$_3$ | CH | |
| CH$_3$ | SO$_2$CH$_3$ | CH$_2$CH$_2$CH$_3$ | OCH$_3$ | OCH$_2$CH$_2$F | CH | |
| CH$_3$ | SO$_2$CH$_2$CH$_3$ | CH$_2$CH$_2$CH$_3$ | Cl | OCH$_3$ | CH | |
| CH$_3$ | SO$_2$CH$_2$CH$_3$ | CH$_2$CH$_3$ | OCH$_3$ | OCH$_3$ | N | |
| H | H | CO$_2$CH$_3$ | CH$_3$ | CH$_2$CH$_3$ | CH | |
| H | H | CO$_2$CH$_3$ | CH$_3$ | OCH$_3$ | CH | |
| H | H | CO$_2$CH$_3$ | OCH$_3$ | OCH$_3$ | CH | |
| H | H | CO$_2$CH$_3$ | CH$_3$ | CH$_3$ | N | |
| H | H | CO$_2$CH$_3$ | CH$_3$ | OCH$_3$ | N | |

TABLE II-continued

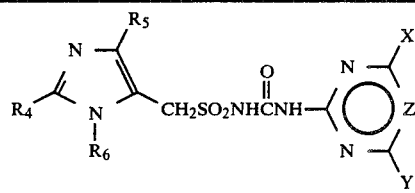

| R4 | R5 | R6 | X | Y | Z | m.p. (°C.) |
|---|---|---|---|---|---|---|
| H | H | CO2CH3 | OCH3 | OCH3 | N | |
| H | H | CO2CH2CH3 | CH3 | CH3 | CH | |
| H | H | CO2CH2CH3 | CH3 | SCH3 | CH | |
| H | H | CO2CH2CH3 | OCH3 | OCH3 | CH | |
| H | H | CO2CH2CH3 | CH3 | CH2CH2CH3 | N | |
| H | H | CO2CH2CH3 | CH3 | OCH3 | N | |
| H | H | CO2CH2CH3 | OCH3 | CH2OCH3 | CH | |
| H | H | SO2N(CH3)2 | CH3 | CH3 | CH | |
| H | H | SO2N(CH3)2 | CH3 | OCH3 | CH | |
| H | H | SO2N(CH3)2 | OCH3 | OCH3 | CH | |
| H | H | SO2N(CH3)2 | CH3 | CH2CH3 | N | |
| H | H | SO2N(CH3)2 | CH3 | OCH3 | N | |
| H | H | SO2N(CH3)2 | OCH3 | OCH3 | N | |
| H | H | SO2N(CH3)CH2CH3 | CH3 | CH3 | CH | |
| H | H | SO2N(CH2CH3)2 | CH3 | OCH3 | CH | |
| H | H | SO2CH3 | OCH3 | OCH3 | CH | |
| H | H | SO2CH3 | CH3 | OCH2CH3 | N | |
| H | H | SO2CH3 | CH3 | OCH3 | N | |
| H | H | SO2CH3 | OCH3 | OCH3 | N | |
| H | H | SO2CH3 | CH3 | CH3 | CH | |
| H | H | SO2CH3 | CH3 | OCH3 | CH | |
| H | H | SO2CH2CH3 | OCH3 | OCH3 | CH | |
| H | H | Cl | OCH3 | CH2CH3 | CH | |
| H | H | SO2CH2CH3 | Cl | OCH2CH2OCH3 | CH | |
| CH3 | H | CO2CH3 | CH3 | CH3 | CH | |
| CH3 | H | CO2CH3 | CH3 | OCH3 | CH | |
| CH3 | H | CO2CH3 | OCH3 | OCH3 | CH | |
| CH3 | H | CO2CH3 | CH3 | CH3 | N | |
| CH3 | H | CO2CH3 | CH3 | OCH3 | N | |
| CH3 | H | CO2CH3 | OCH3 | OCH3 | N | |
| CH3 | H | CO2CH2CH3 | CH3 | CH3 | CH | |
| CH3 | H | CO2CH2CH3 | CH3 | OCH3 | CH | |
| CH3 | H | CO2CH2CH3 | OCH3 | OCH3 | CH | |
| CH3 | H | CO2CH2CH3 | CH3 | CH3 | N | |
| CH3 | H | CO2CH2CH3 | CH3 | OCH3 | N | |
| CH3 | H | CO2CH2CH3 | OCH3 | CH2OCH3 | CH | |
| CH3 | H | SO2N(CH3)2 | CH3 | CH3 | CH | |
| CH3 | H | SO2N(CH3)2 | CH3 | OCH3 | CH | |
| CH3 | H | SO2N(CH3)2 | OCH3 | OCH3 | CH | |
| CH3 | H | SO2N(CH3)2 | CH3 | CH2CH3 | N | |
| CH3 | H | SO2N(CH3)2 | CH3 | OCH3 | N | |
| CH3 | H | SO2N(CH3)2 | OCH3 | OCH3 | N | |
| CH3 | H | SO2N(CH3)CH2CH3 | CH3 | CH3 | CH | |
| CH3 | H | SO2N(CH2CH3)2 | CH3 | OCH3 | CH | |
| CH3 | H | SO2CH3 | OCH3 | OCH3 | CH | |
| CH3 | H | SO2CH3 | CH3 | OCH2CH3 | N | |
| CH3 | H | SO2CH3 | CH3 | OCH3 | N | |
| CH3 | H | SO2CH3 | OCH3 | OCH3 | N | |
| CH3 | H | SO2CH3 | CH3 | CH3 | CH | |
| CH3 | H | SO2CH3 | CH3 | OCH3 | CH | |
| CH3 | H | SO2CH2CH3 | OCH3 | OCH3 | CH | |
| CH3 | H | SO2CH2CH3 | OCH3 | CH2CH3 | CH | |
| CH3 | H | SO2CH2CH3 | Cl | OCH3 | CH | |
| CH3 | NO2 | H | CH3 | OCH3 | CH | |
| CH3 | NO2 | CH3 | CH3 | OCH3 | N | |
| CH3 | NO2 | CH3 | OCH3 | 1,3-dioxolan-2-yl | N | |

TABLE III

[Structure: CH₃-N-C(R₇)=N ring with R₈, connected via CH₂SO₂NHC(O)NH to a pyrimidine/triazine ring with X, Y, Z substituents]

| R₇ | R₈ | X | Y | Z | m.p. (°C.) |
|---|---|---|---|---|---|
| H | CO₂CH₃ | CH₃ | CH₃ | CH | |
| H | CO₂CH₃ | CH₃ | OCH₃ | CH | |
| H | CO₂CH₃ | OCH₃ | OCH₃ | CH | |
| H | CO₂CH₃ | CH₃ | CH₃ | N | |
| H | CO₂CH₃ | CH₃ | OCH₃ | N | |
| H | CO₂CH₃ | OCH₃ | OCH₃ | N | |
| H | CO₂CH₂CH₃ | CH₃ | CH₃ | CH | |
| H | C(O)N(CH₃)₂ | CH₃ | OCH₃ | CH | |
| H | C(O)N(H)C₂H₅ | OCH₃ | OCH₃ | CH | |
| H | SO₂N(CH₃)₂ | OCH₃ | CH₂CH₃ | N | |
| H | SO₂N(CH₃)₂ | CH₃ | OCH₃ | N | |
| H | SO₂N(CH₃)₂ | OCH₃ | OCH₃ | N | |
| H | SO₂N(CH₃)₂ | CH₃ | CH₃ | CH | |
| H | SO₂N(CH₃)₂ | Br | OCH₃ | CH | |
| H | SO₂N(CH₃)₂ | OCH₃ | OCH₃ | CH | |
| H | SO₂N(CH₃)OCH₃ | CH₃ | CH₃ | N | |
| H | SO₂N(CH₃)CH₂CH₃ | CH₃ | OCH₂CH₃ | N | |
| H | SO₂CH₃ | OCH₃ | OCH₃ | N | |
| H | SO₂CH₃ | CH₃ | CH₃ | CH | |
| H | SO₂CH₃ | CH₃ | OCH₃ | CH | |
| H | SO₂CH₃ | OCH₃ | OCH₃ | CH | |
| H | SO₂CH₃ | CH₃ | CH₃ | N | |
| H | SO₂CH₃ | CH₃ | OCH₃ | N | |
| H | SO₂CH₂CH₃ | OCH₃ | SCH₃ | N | |
| H | NO₂ | CH₃ | CH₃ | CH | |
| H | NO₂ | CH₃ | OCH₃ | CH | |
| H | NO₂ | OCH₃ | OCH₃ | CH | |
| H | NO₂ | Cl | OCH₃ | CH | |
| H | NO₂ | OCH₃ | CH₂OCH₃ | CH | |
| CH₃ | CO₂CH₃ | CH₃ | CH₃ | CH | |
| CH₃ | CO₂CH₃ | CH₃ | OCH₃ | CH | |
| CH₃ | CO₂CH₃ | OCH₃ | OCH₃ | CH | |
| CH₃ | CO₂CH₃ | CH₃ | CH₃ | N | |
| CH₃ | CO₂CH₃ | CH₃ | OCH₃ | N | |
| CH₃ | CO₂CH₃ | OCH₃ | OCH₂CH₂F | N | |
| CH₃ | CO₂CH₂CH₃ | CH₃ | CH₃ | CH | |
| CH₃ | CO₂CH₂CH₃ | CH₃ | OCH₃ | CH | |
| CH₃ | CO₂CH₂CH₃ | OCF₂H | OCH₃ | CH | |
| CH₃ | SO₂N(CH₃)₂ | OCH₃ | CH₂CH₃ | N | |
| CH₃ | SO₂N(CH₃)₂ | CH₃ | OCH₃ | N | |
| CH₃ | SO₂N(CH₃)₂ | OCH₃ | OCH₃ | N | |
| CH₃ | SO₂N(CH₃)₂ | CH₃ | CH₃ | CH | |
| CH₃ | SO₂N(CH₃)₂ | CH₃ | OCH₃ | CH | |
| CH₃ | SO₂N(CH₃)₂ | OCH₃ | OCH₃ | CH | |
| CH₃ | SO₂N(CH₃)OCH₃ | CH₃ | CH₃ | N | |
| CH₃ | SO₂N(CH₃)CH₂CH₃ | CH₃ | OCH₂CH₃ | N | |
| CH₃ | SO₂CH₃ | OCH₃ | OCH₃ | N | |
| CH₃ | SO₂CH₃ | CH₃ | CH₃ | CH | |
| CH₃ | SO₂CH₃ | CH₃ | OCH₃ | CH | |
| CH₃ | SO₂CH₃ | OCH₂CF₃ | OCH₃ | CH | |
| CH₃ | SO₂CH₃ | CH₃ | CH₃ | N | |
| CH₃ | SO₂CH₃ | CH₃ | OCH₃ | N | |
| CH₃ | SO₂CH₃ | OCH₃ | OCH₃ | N | |
| CH₃ | NO₂ | CH₃ | CH₃ | CH | |
| CH₃ | NO₂ | CH₃ | Δ | CH | |
| CH₃ | NO₂ | OCH₃ | OCH₃ | CH | |
| CH₃ | NO₂ | Cl | OCH₃ | CH | |
| CH₃ | NO₂ | OCH₃ | CH₂OCH₃ | CH | |
| CH₃ | NO₂ | OCH₃ | 1,3-dioxolan-2-yl | CH | |
| H | CO₂CH₃ | OCH₃ | CH₂F | CH | |
| H | CO₂CH₃ | OCH₃ | C≡CH | CH | |
| H | CO₂CH₃ | OCH₃ | CF₃ | CH | |
| H | CO₂CH₃ | OCH₃ | NHCH₃ | CH | |
| H | CO₂CH₃ | OCH₃ | N(CH₃)₂ | CH | |
| H | CO₂CH₃ | OCH₃ | OCH₂CH=CH₂ | CH | |
| H | CO₂CH₃ | OCH₃ | CH(OCH₂CH₃)₂ | CH | |

TABLE IV

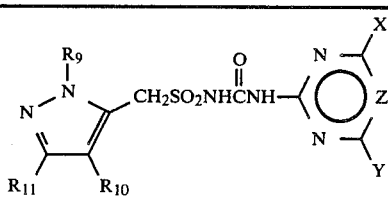

| $R_9$ | $R_{10}$ | $R_{11}$ | X | Y | Z | m.p. (°C.) |
|---|---|---|---|---|---|---|
| H | $CO_2CH_3$ | H | $CH_3$ | $CH_3$ | CH | |
| H | $CO_2CH_3$ | H | $CH_3$ | $OCH_3$ | CH | |
| H | $CO_2CH_3$ | H | $OCH_3$ | $OCH_3$ | CH | |
| H | $CO_2CH_3$ | H | $CH_3$ | $CH_3$ | N | |
| H | $CO_2CH_3$ | H | $CH_3$ | $OCH_3$ | N | |
| H | $CO_2CH_2CH_3$ | H | $OCH_3$ | $OCH_3$ | N | |
| H | $CO_2CH_3$ | $CH_3$ | $CH_3$ | $CF_3$ | CH | |
| $CH_3$ | $CO_2CH_3$ | H | $CH_3$ | $OCH_3$ | CH | |
| $CH_3$ | $CO_2CH_3$ | H | $CH_3$ | $OCH_2CH_3$ | CH | |
| $CH_3$ | $CO_2CH_3$ | H | Cl | $OCH_3$ | CH | |
| $CH_3$ | $CO_2CH_3$ | $CH_3$ | $CH_3$ | $CH_3$ | CH | |
| $CH_3$ | $CO_2CH_3$ | $CH_3$ | $CH_3$ | $OCH_3$ | CH | |
| $CH_3$ | $CO_2CH_3$ | $CH_3$ | $OCH_3$ | $OCH_2CH_2OCH_3$ | CH | |
| $CH_3$ | $CO_2CH_3$ | $CH_3$ | $CH_3$ | $CH_3$ | N | |
| $CH_3$ | $CO_2CH_3$ | $CH_3$ | $CH_3$ | $OCH_3$ | N | |
| $CH_3$ | $CO_2CH_3$ | $CH_3$ | $OCH_3$ | $OCH_3$ | N | |
| $CH_3$ | $C(O)NH_2$ | $CH_3$ | $CH_3$ | $OCH_2CH_3$ | CH | |
| $CH_3$ | $C(O)NHCH_3$ | $CH_3$ | $OCH_3$ | $CH_2OCH_3$ | CH | |
| $CH_3$ | $CO_2CH_3CH$ | H | $CH_3$ | $OCH_3$ | CH | |
| $CH_3$ | $CO_2CH_3CH$ | H | $OCH_3$ | $OCH_3$ | CH | 198–200° |
| $CH_3$ | $CO_2CH_3CH$ | H | $CH_3$ | $OCH_3$ | N | |
| $CH_3$ | $CO_2CH_3CH$ | H | $OCH_3$ | $OCH_3$ | N | 199–201° |
| $CH_3$ | $CO_2CH_3CH$ | H | Cl | $OCH_3$ | CH | |
| $CH_3$ | $CO_2CH_2CH_3$ | $CH_3$ | $OCF_2H$ | $CH_3$ | CH | |
| $CH_3$ | $CO_2CH_2CH_3$ | $CH_3$ | $CH_3$ | $OCH_3$ | CH | |
| $CH_3$ | $CO_2CH_2CH_3$ | $CH_3$ | $OCH_3$ | $OCH_3$ | CH | 190 |
| $CH_3$ | $CO_2CH_2CH_3$ | $CH_3$ | $CH_3$ | $CH_3$ | N | |
| $CH_3$ | $CO_2CH_2CH_3$ | $CH_3$ | $CH_3$ | $OCH_3$ | N | 183–184° |
| $CH_3$ | $CO_2CH_2CH_3$ | $CH_3$ | $OCH_3$ | $OCH_3$ | N | 165–167° |
| $CH_3$ | $CO_2CH_2CH_3$ | $CH_3$ | Cl | $OCH_3$ | CH | 140.5–144.5 |
| $CH_3$ | $CO_2CH_2CH_3$ | $CH_3$ | $OCH_3$ | $OCH_2CH_3$ | CH | |
| $CH_2CH_2CH_3$ | $CO_2CH_2CH_3$ | $CH_3$ | $OCH_3$ | $OCH_3$ | N | |
| $CH_2CH_2CH_3$ | $CO_2CH_2CH_3$ | $CH_3$ | $OCH_3$ | $OCH_3$ | CH | |
| $CH_2CH_2CH_2$ | $CO_2CH_2CH_3$ | $CH_3$ | $CH_3$ | $OCH_3$ | CH | |
| $CH_2CH_2CH_2$ | $CO_2CH_2CH_3$ | H | $OCH_3$ | $CH_2F$ | CH | |
| $CH_2CH_2CH_3$ | $CO_2CH_2CH_3$ | H | $OCH_3$ | $OCH_3$ | N | |
| $CH_2CH_2CH_2$ | $CO_2CH_3$ | H | $OCH_3$ | $OCH_3$ | CH | |
| $CH_2CH_2CH_3$ | $CO_2CH_3$ | $CH_3$ | $OCH_3$ | $OCH_3$ | N | |
| $C_6H_5$ | $CO_2Et$ | H | $OCH_3$ | $OCH_3$ | CH | |
| $C_6H_5$ | $CO_2Et$ | $CH_3$ | $CH_3$ | $CH_3$ | N | |
| $C_6H_5$ | $CO_2Et$ | $CH_3$ | $CH_3$ | $OCH_3$ | N | |
| $C_6H_5$ | $CO_2Et$ | $CH_3$ | $OCH_3$ | $OCH_3$ | N | |
| $C_6H_5$ | $CO_2CH_3$ | $CH_3$ | $CH_3$ | $CH_3$ | CH | |
| $C_6H_5$ | $CO_2Et$ | $CH_3$ | $CH_3$ | $SCH_3$ | CH | |
| $C_6H_5$ | $CO_2Et$ | $CH_3$ | $OCH_3$ | $OCH_3$ | CH | |
| H | $SO_2N(CH_3)_2$ | H | Br | $OCH_3$ | CH | |
| H | $SO_2N(CH_2CH_3)_2$ | H | $OCH_3$ | $OCH_2CH_3$ | N | |
| H | $SO_2N(CH_3)OCH_3$ | H | $CH_3$ | $OCH_3$ | CH | |
| H | $SO_2N(CH_3)_2$ | $CH_3$ | $OCH_3$ | $OCH_3$ | CH | |
| H | $SO_2N(CH_2CH_3)_2$ | $CH_3$ | $CH_3$ | $CH_2F$ | N | |
| H | $SO_2N(OCH_3)CH_3$ | $CH_3$ | $CH_3$ | $OCH_3$ | N | |
| H | $NO_2$ | $CH_3$ | $OCH_3$ | $OCH_3$ | N | |
| $CH_3$ | $SO_2N(CH_3)_2$ | H | $CH_3$ | $CH_3$ | CH | |
| $CH_3$ | $SO_2N(CH_3)_2$ | $CH_3$ | $CH_3$ | $OCH_3$ | CH | |
| $CH_3$ | $SO_2N(CH_3)OCH_3$ | H | $OCH_3$ | $CH(OCH_3)_2$ | CH | |
| $CH_3$ | $SO_2N(CH_3)CH_2CH_3$ | $CH_3$ | $CH_3$ | $CH_3$ | N | |
| $CH_3$ | $NO_2$ | H | $CH_3$ | $OCH_2CH_3$ | N | |
| $CH_3$ | $NO_2$ | $CH_3$ | $OCH_3$ | $OCH_3$ | N | |
| $CH_2CH_2CH_3$ | $SO_2N(CH_3)_2$ | H | $CH_3$ | $CH_3$ | CH | |
| $CH_2CH_2CH_3$ | $SO_2N(CH_3)_2$ | $CH_3$ | $CH_3$ | $OCH_3$ | CH | |
| $CH_2CH_2CH_3$ | $SO_2N(CH_3)OCH_3$ | H | $OCH_3$ | $OCH_3$ | CH | |
| $CH_2CH_2CH_3$ | $SO_2N(CH_3)OCH_3$ | $CH_3$ | $CH_3$ | $CH_3$ | N | |
| $CH_2CH_2CH_3$ | $NO_2$ | H | $CH_3$ | $OCH_3$ | N | |
| $CH_2CH_2CH_3$ | $NO_2$ | $CH_3$ | $OCH_3$ | $OCH_3$ | N | |
| $C_6H_5$ | $SO_2N(CH_3)_2$ | H | $CH_3$ | $CH_3$ | CH | |
| $C_6H_5$ | $SO_2N(CH_3)CH_2CH_3$ | $CH_3$ | $CH_3$ | $OCH_3$ | CH | |
| $C_6H_5$ | $SO_2N(CH_3)OCH_3$ | H | $OCH_3$ | $OCH_3$ | CH | |
| $C_6H_5$ | $SO_2N(CH_3)OCH_3$ | $CH_3$ | $CH_3$ | $CH_2CH_3$ | N | |
| $C_6H_5$ | $NO_2$ | H | $CH_3$ | $OCH_3$ | N | |
| $C_6H_5$ | $NO_2$ | $CH_3$ | $OCH_3$ | $OCH_3$ | N | |
| $C_6H_5$ | $NO_2$ | $CH_3$ | $CH_3$ | $CH_3$ | CH | |

TABLE IV-continued

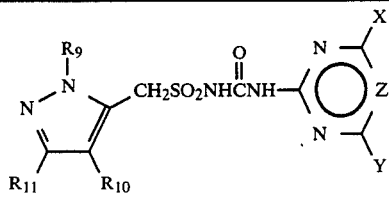

| R9 | R10 | R11 | X | Y | Z | m.p. (°C.) |
|---|---|---|---|---|---|---|
| H | SO2CH2CH3 | H | CH3 | N(CH3)2 | N | |
| H | SO2CH2CH3 | CH3 | OCH3 | OCH3 | N | |
| CH3 | SO2CH2CH3 | H | OCH2CF3 | CH3 | CH | |
| CH2CH3 | SO2CH2CH3 | CH3 | CH3 | OCH3 | CH | |
| CH(CH3)2 | SO2CH2CH3 | H | OCH3 | OCH3 | CH | |
| C6H5 | SO2CH2CH3 | CH3 | CH3 | CH2CH2CH3 | N | |

TABLE V

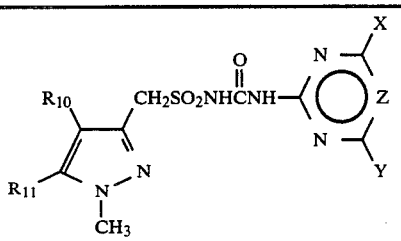

| R10 | R11 | X | Y | Z | m.p. (°C.) |
|---|---|---|---|---|---|
| CO2CH3 | H | CH3 | CH3 | CH | |
| CO2CH3 | H | CH3 | OCH3 | CH | |
| CO2CH3 | H | OCH3 | OCH3 | CH | |
| CO2CH3 | H | Cl | OCH3 | CH | |
| CO2CH3 | H | CH3 | OCH3 | N | |
| CO2CH3 | H | OCH3 | OCH3 | N | |
| CO2CH3 | CH3 | CH3 | CH3 | CH | |
| CO2CH3 | CH3 | CH3 | OCH3 | CH | |
| CO2CH3 | CH3 | OCH3 | OCH3 | CH | |
| CO2CH3 | CH3 | CH3 | OCH2CH3 | CH | |
| CO2CH3 | CH3 | CH3 | OCH3 | N | |
| CO2CH3 | CH3 | OCH3 | OCH3 | N | |
| CO2Et | H | CH3 | CH3 | CH | |
| CO2Et | CH3 | CH3 | OCH3 | CH | |
| CO2Et | CH3 | OCH3 | OCH3 | CH | 180–183 |
| CO2Et | CH3 | Br | OCH3 | CH | |
| CO2Et | CH3 | CH3 | OCH2CH3 | CH | |
| CO2Et | CH3 | CH3 | CH3 | N | |
| CO2Et | CH3 | CH3 | OCH3 | N | 154–157° |
| CO2Et | CH3 | OCH3 | OCH3 | N | 188–188.5° |
| CO2Et | CH3 | OCH3 | OCH2CH3 | N | |
| CO2Et | CH3 | CH3 | CH2OCH3 | CH | |
| CO2Et | CH3 | OCH3 | CH2OCH3 | CH | |
| SO2N(CH3)2 | H | OCF2H | CH3 | CH | |
| SO2N(CH3)2 | H | CH3 | OCH3 | CH | |
| SO2N(CH3)2 | H | OCH3 | OCH3 | CH | |
| SO2N(CH3)2 | H | CH3 | CH3 | N | |
| SO2N(CH3)2 | H | CH3 | OCH3 | N | |
| SO2NCH3(OCH3)2 | H | OCH3 | OCH3 | N | |
| SO2N(CH2CH3)2 | CH3 | CH3 | CH3 | CH | |
| SO2N(CH2CH3)2 | H | CH3 | OCH3 | CH | |
| SO2N(CH2CH3)2 | H | OCH3 | OCH3 | CH | |
| SO2N(CH2CH3)2 | H | CH3 | CH3 | N | |
| SO2N(CH2CH3)2 | H | CH3 | OCH3 | N | |
| SO2N(CH3)CH2CH3 | H | OCH3 | OCH3 | N | |
| SO2CH3 | H | CH3 | CH3 | CH | |
| SO2CH3 | H | OCH3 | OCH3 | CH | |
| SO2CH3 | H | OCH3 | CH3 | N | |
| SO2CH3 | H | CH3 | NHCH3 | N | |
| SO2CH3 | CH3 | OCH2CF3 | OCH3 | N | |
| SO2CH3 | CH3 | OCH3 | OCH3 | N | |
| SO2CH2CH3 | H | OCH3 | OCH3 | CH | |
| SO2CH2CH3 | H | CH3 | OCH3 | CH | |
| SO2CH2CH3 | CH3 | OCH3 | OCH3 | CH | |
| SO2CH2CH3 | CH3 | CH3 | CH3 | N | |
| SO2CH2CH3 | CH3 | CH3 | OCH3 | N | |

TABLE V-continued

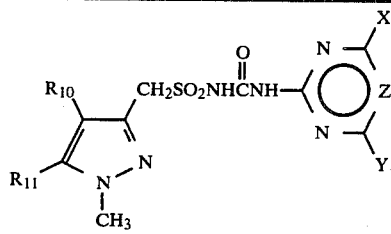

| R10 | R11 | X | Y | Z | m.p. (°C.) |
|---|---|---|---|---|---|
| SO2CH2CH3 | CH3 | OCH3 | OCH3 | N | |
| SO2CH2CH3 | CH3 | OCH3 | CH2CH3 | CH | |
| SO2CH2CH3 | CH3 | CH3 | OCH2CH3 | CH | |
| SO2CH2CH3 | CH3 | Cl | OCH3 | CH | |
| NO2 | H | OCH3 | CH3 | CH | |
| NO2 | H | OCH3 | CH3 | N | |
| NO2 | H | OCH3 | OCH2C≡CH | CH | |

TABLE VI

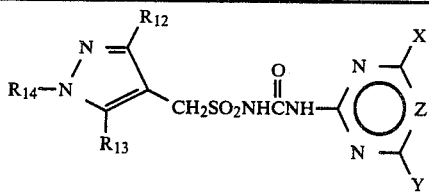

| R12 | R13 | R14 | X | Y | Z | m.p. (°C.) |
|---|---|---|---|---|---|---|
| CO2CH3 | H | H | CH3 | OCH3 | CH | |
| CO2CH3 | H | H | OCH3 | OCH3 | CH | |
| CO2CH3 | H | H | CH3 | CH3 | N | |
| CO2CH3 | H | H | CH3 | OCH3 | N | |
| CO2CH3 | H | H | OCH3 | OCH3 | N | |
| CO2CH3 | H | H | CH3 | CH3 | CH | |
| CO2CH2CH3 | H | H | CH3 | OCH3 | CH | |
| CO2CH2CH3 | H | H | OCH2CF3 | OCH3 | CH | |
| CO2CH2CH3 | H | H | CH3 | CH3 | N | |
| CO2CH2CH3 | H | H | CH3 | OCH3 | N | |
| CO2CH2CH3 | H | H | OCH3 | OCH3 | N | |
| C(O)N(CH3)2 | H | H | OCF2H | CH3 | CH | |
| C(O)NHC2H5 | H | H | CH3 | CH3 | CH | |
| SO2N(CH3)2 | H | H | CH3 | OCH3 | CH | |
| SO2N(CH3)2 | H | H | OCH3 | OCH3 | CH | |
| SO2N(CH3)2 | H | H | CH3 | CH3 | N | |
| SO2N(CH3)2 | H | H | CH3 | OCH3 | N | |
| SO2N(CH3)2 | H | H | OCH3 | OCH3 | N | |
| SO2N(CH3)2 | H | H | OCH3 | CH2CH3 | N | |
| SO2N(CH3)OCH3 | H | H | OCH3 | OCH2CH3 | CH | |
| SO2N(CH3)OCH3 | H | H | Cl | OCH3 | CH | |
| SO2N(CH3)OCH3 | H | H | OCH3 | CH2OCH3 | CH | |
| CO2CH3 | H | CH3 | CH3 | OCH3 | CH | |
| CO2CH3 | H | CH3 | OCH3 | OCH3 | CH | |
| CO2CH3 | H | CH3 | CH3 | CH3 | N | |
| CO2CH3 | H | CH3 | CH3 | OCH3 | N | |
| CO2CH3 | H | CH3 | OCH3 | OCH3 | N | |
| CO2CH3 | H | CH3 | CH3 | CH3 | CH | |
| CO2CH2CH3 | H | CH3 | CH3 | CH3 | CH | |
| CO2CH2CH3 | H | CH3 | CH3 | OCH3 | CH | |
| CO2CH2CH3 | H | CH3 | OCH3 | OCH3 | CH | |
| CO2CH2CH3 | H | CH3 | CH3 | CH3 | N | |
| CO2CH2CH3 | H | CH3 | CH3 | OCH3 | N | |
| CO2CH2CH3 | H | CH3 | OCH3 | OCH3 | N | |
| SO2N(CH3)2 | H | CH3 | CH3 | OCH3 | CH | |
| SO2N(CH3)2 | H | CH3 | OCH3 | OCH3 | CH | |
| SO2N(CH3)2 | H | CH3 | CH3 | CH3 | N | |
| SO2N(CH3)2 | H | CH3 | CH3 | OCH3 | N | |
| SO2N(CH3)2 | H | CH3 | OCH3 | OCH3 | N | |
| SO2N(CH3)2 | H | CH3 | OCH3 | CH2CH3 | N | |
| SO2N(CH3)OCH3 | H | CH3 | OCH3 | OCH2CH2F | CH | |
| SO2N(CH3)OCH3 | H | CH3 | Cl | OCH3 | CH | |
| SO2N(CH3)OCH3 | H | CH3 | OCH3 | CH2OCH3 | CH | |
| SO2N(CH2CH3)2 | H | CH3 | OCH3 | OCH3 | CH | |
| SO2CH3 | H | CH3 | OCH3 | CH3 | CH | |
| SO2CH2CH3 | H | CH3 | OCH3 | OCH3 | N | |
| NO2 | H | CH3 | OCH3 | OCH2CH3 | CH | |

TABLE VI-continued

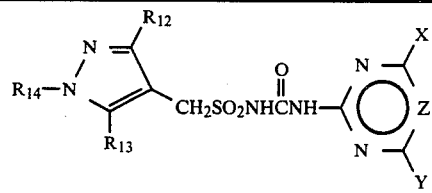

| $R_{12}$ | $R_{13}$ | $R_{14}$ | X | Y | Z | m.p. (°C.) |
|---|---|---|---|---|---|---|
| $SO_2CH_3$ | H | H | $OCH_3$ | $OCH_3$ | N | |
| $SO_2CH_2CH_3$ | H | H | $OCH_3$ | $CH_2OCH_3$ | CH | |
| $NO_2$ | H | H | $OCH_3$ | $OCH_3$ | N | |
| $NO_2$ | H | H | $OCH_3$ | Δ | N | |
| H | $CO_2CH_3$ | H | $CH_3$ | $OCH_3$ | CH | |
| H | $CO_2CH_3$ | H | $OCH_3$ | $OCH_3$ | CH | |
| H | $CO_2CH_3$ | H | $CH_3$ | $CH_3$ | N | |
| H | $CO_2CH_3$ | H | $OCH_3$ | $OCH_3$ | N | |
| H | $CO_2CH_3$ | H | $CH_3$ | $CH_2F$ | CH | |
| H | $CO_2CH_2CH_3$ | H | $CH_3$ | $OCH_3$ | CH | |
| H | $CO_2CH_2CH_3$ | H | $OCH_3$ | $OCH_3$ | CH | |
| H | $CO_2CH_2CH_3$ | H | $CH_3$ | $CH_3$ | N | |
| H | $CO_2CH_2CH_3$ | H | $CH_3$ | $OCH_3$ | N | |
| H | $CO_2CH_2CH_3$ | H | $OCH_3$ | $OCH_3$ | N | |
| H | $CO_2CH_2CH_3$ | H | $CH_3$ | $CH_3$ | CH | |
| H | $SO_2N(CH_3)_2$ | H | $CH_3$ | $OCH_3CH_2OCH_3$ | CH | |
| H | $SO_2N(CH_3)_2$ | H | $OCH_3$ | $OCH_3$ | CH | |
| H | $SO_2N(CH_3)_2$ | H | $CH_3$ | $CH_3$ | N | |
| H | $SO_2N(CH_3)_2$ | H | $CH_3$ | $N(CH_3)_2$ | N | |
| H | $SO_2N(CH_3)_2$ | H | $OCH_3$ | $OCH_3$ | N | |
| H | $SO_2N(CH_3)_2$ | H | $OCH_3$ | $CH_2CH_3$ | N | |
| H | $SO_2N(CH_3)OCH_3$ | H | $OCH_3$ | $OCH_2CH_3$ | CH | |
| H | $SO_2N(CH_3)OCH_3$ | H | Cl | $OCH_3$ | CH | |
| H | $SO_2N(CH_3)OCH_3$ | H | $OCH_3$ | $CH_2OCH_3$ | CH | |
| H | $CO_2CH_3$ | $CH_3$ | $CH_3$ | $OCH_2C\equiv CH$ | CH | |
| H | $CO_2CH_3$ | $CH_3$ | $OCH_3$ | $OCH_3$ | CH | |
| H | $CO_2CH_3$ | $CH_3$ | $CH_3$ | $CH_3$ | N | |
| H | $CO_2CH_3$ | $CH_3$ | $CH_3$ | $OCH_3$ | N | |
| H | $CO_2CH_3$ | $CH_3$ | $OCH_3$ | $OCH_3$ | N | |
| H | $CO_2CH_3$ | $CH_3$ | $CH_3$ | Δ | CH | |
| H | $CO_2CH_2CH_3$ | $CH_3$ | $CH_3$ | $CF_3$ | CH | |
| H | $CO_2CH_2CH_3$ | $CH_3$ | $CH_3$ | $OCH_3$ | CH | |
| H | $CO_2CH_2CH_3$ | $CH_3$ | $OCH_3$ | $OCH_3$ | CH | |
| H | $CO_2CH_2CH_3$ | $CH_3$ | $CH_3$ | $CH_3$ | N | |
| H | $C(O)N(CH_3)_2$ | $CH_3$ | $CH_3$ | $CH_2CH_2CH_3$ | N | |
| H | $C(O)NH_2$ | $CH_3$ | $OCH_3$ | $OCH_3$ | N | |
| H | $SO_2N(CH_3)_2$ | $CH_3$ | $CH_3$ | $OCH_3$ | CH | |
| H | $SO_2N(CH_3)_2$ | $CH_3$ | $OCH_3$ | $OCH_3$ | CH | |
| H | $SO_2N(CH_3)_2$ | $CH_3$ | $CH_3$ | $CH_3$ | N | |
| H | $SO_2N(CH_3)_2$ | $CH_3$ | $CH_3$ | $OCH_3$ | N | |
| H | $SO_2N(CH_3)_2$ | $CH_3$ | $OCH_3$ | $OCH_3$ | N | |
| H | $SO_2N(CH_3)_2$ | $CH_3$ | $OCH_3$ | $CH_2CH_3$ | N | |
| H | $SO_2N(CH_3)OCH_3$ | $CH_3$ | $OCH_3$ | $OCH_2CH_3$ | CH | |
| H | $SO_2N(CH_3)OCH_3$ | $CH_3$ | Cl | $OCH_3$ | CH | |
| H | $SO_2N(CH_3)OCH_3$ | $CH_3$ | $OCH_3$ | $CH_2OCH_3$ | CH | |
| H | $SO_2N(CH_2CH_3)_2$ | $CH_3$ | $OCH_3$ | $OCH_3$ | CH | |
| H | $SO_2CH_3$ | $CH_3$ | $OCH_3$ | $CH_3$ | CH | |
| H | $SO_2CH_2CH_3$ | $CH_3$ | $OCH_3$ | $OCH_3$ | N | |
| H | $NO_2$ | $CH_3$ | $OCH_3$ | $OCH_2CH_3$ | CH | |
| H | $SO_2CH_3$ | H | $OCH_3$ | $OCH_3$ | N | |
| H | $SO_2CH_2CH_3$ | H | $OCH_3$ | $CH_2OCH_3$ | CH | |
| H | $NO_2$ | H | $OCH_3$ | $SCH_3$ | N | |
| H | $NO_2$ | H | $OCH_3$ | 1,3-dioxolan-2-yl | CH | |

TABLE VII

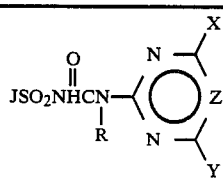

| J | $R_5$ | $R_{19}$ | R | X | Y | Z | m.p. (°C.) |
|---|---|---|---|---|---|---|---|
| J-7 | H | $CH_3$ | H | $OCH_3$ | $CH_3$ | CH | |
| J-7 | H | Cl | H | $OCH_3$ | $CH_3$ | CH | |
| J-7 | H | $NO_2$ | H | $OCH_3$ | $CH_3$ | CH | |

TABLE VII-continued

| J | R5 | R19 | R | X | Y | Z | m.p. (°C.) |
|---|---|---|---|---|---|---|---|
| J-7 | H | SCH2CH3 | H | OCH3 | N(CH3)2 | CH | |
| J-7 | H | SO2CH3 | H | OCH2CF3 | CH3 | N | |
| J-7 | CH3 | SO2CH2CH3 | H | CH3 | C≡CH | N | |
| J-7 | CO2CH3 | H | H | OCH3 | OCH3 | CH | 192–194 |
| J-7 | CO2CH3 | H | H | CH3 | OCH3 | CH | 155–162 |
| J-7 | CO2CH3 | H | H | CH3 | CH3 | CH | 153–156 |
| J-7 | CO2CH3 | H | H | OCH3 | OCH3 | N | 167–169 |
| J-7 | CO2CH3 | H | H | CH3 | OCH3 | N | 166–167 |
| J-7 | CO2CH3 | H | H | Cl | OCH3 | CH | 185–186 |
| J-7 | CO2CH3 | H | CH3 | OCH3 | OCH3 | N | 165–166 |
| J-7 | Cl | H | H | OCH3 | CH2CH2CH3 | CH | |
| J-7 | Cl | CH3 | H | OCH3 | OCH2CH3 | CH | |
| J-7 | SO2N(CH3)2 | H | H | OCH3 | CF3 | CH | |
| J-7 | SO2N(CH3)2 | H | H | OCH3 | SCH3 | CH | |
| J-7 | SO2CH3 | Cl | H | OCH3 | CH(OCH3)2 | CH | |
| J-7 | SO2CH3 | H | H | OCH3 | OCH2CH=CH2 | CH | |
| J-7 | SO2CH2CH3 | H | H | OCHF2 | CH3 | CH | |
| J-8 | H | — | H | OCH3 | CH3 | CH | |
| J-8 | CH3 | — | H | OCH3 | CH3 | N | |
| J-8 | CO2CH3 | — | H | OCH3 | CH3 | CH | |
| J-8 | CO2CH3 | — | H | OCH3 | CH3 | N | |
| J-8 | Cl | — | H | OCH3 | OCH2CH2F | CH | |
| J-8 | SO2N(CH3)2 | — | H | OCH3 | OCH2CH3 | N | |
| J-8 | SO2CH3 | — | H | OCH3 | CH3 | CH | |
| J-8 | NO2 | — | H | OCH3 | NHCH3 | CH | |
| J-9 | H | Br | H | OCF2H | CH3 | CH | |
| J-9 | H | CH3 | H | CH3 | OCH3 | N | |
| J-9 | CH3 | NO2 | H | OCH3 | OCF2H | CH | |
| J-9 | Cl | SCH3 | H | CH3 | OCH3 | N | |
| J-9 | CO2CH3 | Cl | H | Cl | OCH3 | CH | |
| J-9 | CO2CH3 | CH3 | H | OCH3 | OCH3 | N | |
| J-9 | CO2CH3 | SO2CH3 | H | Br | OCH3 | CH | |
| J-9 | SO2N(CH3)2 | H | H | CH3 | CH3 | N | |
| J-9 | SO2CH3 | H | H | OCH3 | CH2CH3 | CH | |
| J-9 | SO2CH2CH3 | H | H | OCH3 | Δ | N | |
| J-10 | H | SO2CH2CH3 | H | OCH3 | CH3 | CH | |
| J-10 | H | NO2 | H | OCH3 | CH3 | N | |
| J-10 | CH3 | Cl | H | OCH3 | CH2OCH3 | CH | |
| J-10 | Cl | Cl | H | OCH3 | OCH3 | N | |
| J-10 | CO2CH3 | SCH3 | H | OCH3 | OCH3 | CH | |
| J-10 | CO2CH3 | H | H | OCH3 | OCH3 | N | |
| J-10 | CO2CH2CH3 | H | H | OCH3 | CH(OEt)2 | N | |
| J-10 | SO2N(CH3)Et | H | H | OCH3 | OCH3 | N | |
| J-10 | SO2CH3 | H | CH3 | OCH3 | OCH3 | CH | |
| J-10 | SO2CH3 | CH3 | H | OCH3 | OCH3 | N | |
| J-11 | Cl | — | H | OCH3 | OCH3 | CH | |
| J-11 | Br | — | H | OCH3 | OCH3 | N | |
| J-11 | CH3 | — | H | OCH3 | OCH2C≡CH | CH | |
| J-11 | CO2CH3 | — | H | OCH3 | CH3 | N | |
| J-11 | CO2CH3 | — | H | OCH3 | CF3 | CH | |
| J-11 | CO2CH2CH3 | — | H | OCH3 | OCH3 | N | |
| J-11 | SO2N(CH3)2 | — | H | CH3 | C≡CH | CH | |
| J-11 | SO2CH3 | — | H | CH3 | N(CH3)2 | N | |
| J-11 | SO2CH2CH3 | — | H | CH3 | CH2F | CH | |

TABLE VIII

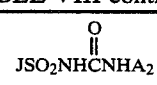

| J | R4 | R5 | R6 | R19 | X1 | Y1 |
|---|---|---|---|---|---|---|
| J2 | H | CH3 | CH3 | — | CH3 | O |
| J2 | CH3 | Cl | CH3 | — | OCH3 | CH2 |
| J2 | H | Br | CH2CH2CH3 | — | OCH3 | O |
| J2 | CH3 | CO2CH3 | CH2CH2CH3 | — | OCH3 | O |
| J2 | CH3 | SO2N(CH3)2 | CH3 | — | CH3 | O |
| J2 | CH3 | H | SO2CH3 | — | OCH3 | CH2 |
| J2 | CH3 | SO2CH2CH3 | CH3 | — | CH3 | O |
| J7 | — | CH3 | — | SCH3 | OCH3 | O |
| J7 | — | Cl | — | CH3 | OCH3 | CH2 |
| J7 | — | CO2CH3 | — | CH3 | CH3 | O |
| J7 | — | H | — | SO2CH3 | OCH3 | O |
| J7 | — | SO2CH3 | — | Cl | OCH3 | O |
| J7 | — | SO2N(CH3)2 | — | H | CH3 | O |
| J8 | — | CH3 | — | — | OCH3 | CH2 |
| J8 | — | Cl | — | — | CH3 | O |
| J8 | — | CO2CH3 | — | — | OCH3 | O |

TABLE VIII-continued $$JSO_2NHCNHA_2$$ with C=O

| J | R$_4$ | R$_5$ | R$_6$ | R$_{19}$ | X$_1$ | Y$_1$ |
|---|---|---|---|---|---|---|
| J$_8$ | — | CO$_2$CH$_2$CH$_3$ | — | — | OCH$_2$CH$_3$ | O |
| J$_8$ | — | NO$_2$ | — | — | CH$_3$ | O |
| J$_8$ | — | SO$_2$CH$_3$ | — | — | OCF$_2$H | CH$_2$ |
| J$_8$ | — | SO$_2$CH$_3$ | — | — | OCH$_3$ | CH$_2$ |
| J$_9$ | — | Cl | — | CH$_3$ | OCH$_3$ | O |
| J$_9$ | — | CO$_2$CH$_3$ | — | CH$_3$ | OCH$_3$ | O |
| J$_9$ | — | SO$_2$CH$_2$CH$_3$ | — | CH$_3$ | CH$_3$ | O |
| J$_{10}$ | — | SO$_2$CH$_3$ | — | CH$_3$ | CH$_3$ | O |
| J$_{10}$ | — | Cl | — | CH$_3$ | OCH$_3$ | CH$_2$ |
| J$_{10}$ | — | CO$_2$CH$_3$ | — | SCH$_3$ | OCH$_3$ | O |
| J$_{10}$ | — | SO$_2$CH$_3$ | — | Cl | CH$_3$ | CH$_2$ |
| J$_{11}$ | — | Cl | — | — | OCH$_3$ | O |
| J$_{11}$ | — | CO$_2$CH$_3$ | — | — | OCH$_3$ | O |
| J$_{11}$ | — | SO$_2$N(CH$_3$)$_2$ | — | — | OCH$_3$ | CH$_2$ |
| J$_{11}$ | — | SO$_2$CH$_3$ | — | — | CH$_3$ | O |

TABLE IX $$JSO_2NHCNHA_2$$ with C=O

| J | R$_1$ | R$_2$ | R$_3$ | R$_7$ | R$_8$ | X$_1$ | Y$_1$ |
|---|---|---|---|---|---|---|---|
| J$_1$ | CH$_3$ | H | H | — | — | CH$_3$ | O |
| J$_1$ | CH$_3$ | CH$_3$ | CH$_3$ | — | — | OCH$_3$ | CH$_2$ |
| J$_1$ | CO$_2$CH$_3$ | CH$_3$ | CH$_3$ | — | — | CH$_3$ | CH$_2$ |
| J$_1$ | CO$_2$CH$_3$ | H | H | — | — | OCH$_3$ | O |
| J$_1$ | CO$_2$CH$_3$ | H | H | — | — | OCF$_2$H | CH$_2$ |
| J$_1$ | CO$_2$CH$_3$ | CH$_3$ | H | — | — | OCH$_3$ | O |
| J$_1$ | CO$_2$CH$_2$CH$_3$ | H | H | — | — | CH$_3$ | O |
| J$_1$ | CO$_2$CH$_2$CH$_3$ | CH$_3$ | H | — | — | CH$_3$ | O |
| J$_1$ | SO$_2$N(CH$_3$)$_2$ | H | H | — | — | CH$_3$ | O |
| J$_1$ | SO$_2$N(CH$_3$)$_2$ | CH$_3$ | CH$_3$ | — | — | OCH$_2$CH$_3$ | CH$_2$ |
| J$_1$ | SO$_2$N(CH$_2$CH$_3$)$_2$ | H | H | — | — | OCH$_3$ | O |
| J$_1$ | SO$_2$CH$_3$ | H | H | — | — | OCH$_3$ | CH$_2$ |
| J$_1$ | SO$_2$CH$_3$ | H | CH$_3$ | — | — | OCH$_3$ | O |
| J$_1$ | SO$_2$CH$_3$ | CH$_3$ | CH$_3$ | — | — | CH$_3$ | O |
| J$_1$ | SO$_2$CH$_2$CH$_3$ | CH$_3$ | CH$_3$ | — | — | CH$_3$ | CH$_2$ |
| J$_3$ | — | — | — | H | CO$_2$CH$_3$ | CH$_3$ | O |
| J$_3$ | — | — | — | H | CO$_2$CH$_2$CH$_3$ | CH$_3$ | O |
| J$_3$ | — | — | — | CH$_3$ | SO$_2$N(CH$_3$)$_2$ | OCH$_3$ | CH$_2$ |
| J$_3$ | — | — | — | CH$_3$ | SO$_2$N(OCH$_3$)CH$_3$ | OCH$_3$ | CH$_2$ |
| J$_3$ | — | — | — | H | SO$_2$CH$_3$ | OCH$_3$ | O |
| J$_3$ | — | — | — | H | SO$_2$CH$_3$ | OCH$_3$ | CH$_2$ |
| J$_3$ | — | — | — | CH$_3$ | SO$_2$CH$_2$CH$_3$ | CH$_3$ | O |
| J$_3$ | — | — | — | CH$_3$ | NO$_2$ | CH$_3$ | O |

TABLE X $$JSO_2NHCNHA_2$$ with C=O

| J | R$_9$ | R$_{10}$ | R$_{11}$ | R$_{12}$ | R$_{13}$ | R$_{14}$ | X$_1$ | Y$_1$ |
|---|---|---|---|---|---|---|---|---|
| J$_4$ | H | CO$_2$CH$_3$ | H | — | — | — | OCH$_3$ | CH$_2$ |
| J$_4$ | CH$_3$ | CO$_2$CH$_3$ | CH$_3$ | — | — | — | CH$_3$ | O |
| J$_4$ | CH$_3$ | CO$_2$CH$_3$ | CH$_3$ | — | — | — | CH$_3$ | O |
| J$_4$ | CH$_3$ | CO$_2$CH$_2$CH$_3$ | H | — | — | — | OCH$_3$ | O |
| J$_4$ | CH$_3$ | SO$_2$N(CH$_3$)$_2$ | CH$_3$ | — | — | — | OCH$_3$ | O |
| J$_4$ | CH$_3$ | SO$_2$N(OCH$_3$)CH$_3$ | CH$_3$ | — | — | — | OCH$_2$CH$_3$ | CH$_2$ |
| J$_4$ | CH$_3$ | SO$_2$CH$_3$ | CH$_3$ | — | — | — | CH$_3$ | O |
| J$_4$ | CH$_3$ | SO$_2$CH$_3$ | CH$_3$ | — | — | — | OCF$_2$H | O |
| J$_4$ | CH$_2$CH$_2$CH$_3$ | CO$_2$CH$_3$ | CH$_3$ | — | — | — | OCH$_3$ | CH$_2$ |
| J$_4$ | CH$_3$ | NO$_2$ | CH$_3$ | — | — | — | OCH$_3$ | O |
| J$_4$ | CH$_3$ | SO$_2$CH$_2$CH$_3$ | H | — | — | — | CH$_3$ | O |
| J$_4$ | Ph | CO$_2$CH$_3$ | H | — | — | — | OCH$_3$ | CH$_2$ |
| J$_5$ | — | CO$_2$CH$_3$ | H | — | — | — | OCH$_3$ | O |
| J$_5$ | — | CO$_2$CH$_3$ | CH$_3$ | — | — | — | OCH$_3$ | O |
| J$_5$ | — | CO$_2$H | H | — | — | — | CH$_3$ | O |
| J$_5$ | — | SO$_2$N(CH$_3$)$_2$ | H | — | — | — | OCH$_3$ | CH$_2$ |
| J$_5$ | — | SO$_2$N(CH$_3$)Et | H | — | — | — | OCH$_3$ | O |
| J$_5$ | — | SO$_2$CH$_3$ | CH$_3$ | — | — | — | CH$_3$ | O |
| J$_5$ | — | SO$_2$CH$_3$ | CH$_3$ | — | — | — | OCH$_3$ | O |
| J$_5$ | — | SO$_2$CH$_2$CH$_3$ | CH$_3$ | — | — | — | OCH$_3$ | CH$_2$ |
| J$_5$ | — | NO$_2$ | H | — | — | — | OCH$_3$ | O |
| J$_6$ | — | — | — | H | CO$_2$CH$_3$ | H | CH$_3$ | O |
| J$_6$ | — | — | — | H | CO$_2$CH$_3$ | CH$_3$ | OCH$_3$ | CH$_2$ |
| J$_6$ | — | — | — | CH$_3$ | H | CH$_3$ | CH$_3$ | O |
| J$_6$ | — | — | — | H | SO$_2$N(CH$_3$)$_2$ | CH$_3$ | OCH$_3$ | O |
| J$_6$ | — | — | — | NO$_2$ | H | CH$_3$ | OCH$_3$ | O |
| J$_6$ | — | — | — | H | SO$_2$CH$_3$ | CH$_3$ | OCH$_3$ | CH$_2$ |
| J$_6$ | — | — | — | CO$_2$CH$_3$ | H | H | CH$_3$ | O |

TABLE X-continued $$\underset{JSO_2NHCNHA_2}{\overset{O}{\parallel}}$$

| J | R$_9$ | R$_{10}$ | R$_{11}$ | R$_{12}$ | R$_{13}$ | R$_{14}$ | X$_1$ | Y$_1$ |
|---|---|---|---|---|---|---|---|---|
| J$_6$ | — | — | — | CO$_2$CH$_3$ | H | CH$_3$ | CH$_3$ | O |
| J$_6$ | — | — | — | SO$_2$CH$_3$ | H | CH$_3$ | OCH$_3$ | CH$_2$ |

TABLE XI $$\underset{JSO_2NHCNHA_3}{\overset{O}{\parallel}}$$

| J | R$_1$ | R$_2$ | R$_3$ | R$_7$ | R$_8$ | X$_1$ |
|---|---|---|---|---|---|---|
| J$_1$ | CH$_3$ | H | H | — | — | CH$_3$ |
| J$_1$ | CH$_3$ | CH$_3$ | CH$_3$ | — | — | OCH$_3$ |
| J$_1$ | CO$_2$CH$_3$ | CH$_3$ | CH$_3$ | — | — | CH$_3$ |
| J$_1$ | CO$_2$CH$_3$ | H | H | — | — | OCH$_3$ |
| J$_1$ | CO$_2$CH$_3$ | H | H | — | — | OCF$_2$H |
| J$_1$ | CO$_2$CH$_3$ | CH$_3$ | H | — | — | OCH$_3$ |
| J$_1$ | CO$_2$CH$_2$CH$_3$ | H | H | — | — | CH$_3$ |
| J$_1$ | CO$_2$CH$_2$CH$_3$ | CH$_3$ | H | — | — | CH$_3$ |
| J$_1$ | SO$_2$N(CH$_3$)$_2$ | H | H | — | — | CH$_3$ |
| J$_1$ | SO$_2$N(CH$_3$)$_2$ | H | CH$_3$ | — | — | OCH$_3$ |
| J$_1$ | SO$_2$N(CH$_3$)$_2$ | CH$_3$ | CH$_3$ | — | — | OCH$_2$CH$_3$ |
| J$_1$ | SO$_2$N(CH$_2$CH$_3$)$_2$ | H | H | — | — | OCH$_3$ |
| J$_1$ | SO$_2$CH$_3$ | H | H | — | — | OCH$_3$ |
| J$_1$ | SO$_2$CH$_3$ | H | CH$_3$ | — | — | OCH$_3$ |
| J$_1$ | SO$_2$CH$_3$ | CH$_3$ | CH$_3$ | — | — | CH$_3$ |
| J$_1$ | SO$_2$CH$_2$CH$_3$ | CH$_3$ | CH$_3$ | — | — | CH$_3$ |
| J$_3$ | — | — | — | H | CO$_2$CH$_3$ | CH$_3$ |
| J$_3$ | — | — | — | H | CO$_2$CH$_2$CH$_3$ | CH$_3$ |
| J$_3$ | — | — | — | H | SO$_2$N(CH$_3$)$_2$ | OCH$_3$ |
| J$_3$ | — | — | — | CH$_3$ | SO$_2$N(OCH$_3$)CH$_3$ | OCH$_3$ |
| J$_3$ | — | — | — | H | SO$_2$CH$_3$ | OCH$_3$ |
| J$_3$ | — | — | — | H | SO$_2$CH$_3$ | OCH$_2$CH$_3$ |
| J$_3$ | — | — | — | CH$_3$ | SO$_2$CH$_3$ | CH$_3$ |
| J$_3$ | — | — | — | CH$_3$ | NO$_2$ | CH$_3$ |

TABLE XII $$\underset{JSO_2NHCNHA_3}{\overset{O}{\parallel}}$$

| J | R$_4$ | R$_5$ | R$_6$ | R$_{19}$ | X$_1$ |
|---|---|---|---|---|---|
| J$_2$ | H | CH$_3$ | CH$_3$ | — | CH$_3$ |
| J$_2$ | CH$_3$ | Cl | CH$_3$ | — | OCH$_3$ |
| J$_2$ | H | Br | CH$_2$CH$_2$CH$_3$ | — | OCF$_2$H |
| J$_2$ | CH$_3$ | CO$_2$CH$_3$ | CH$_3$ | — | OCH$_3$ |
| J$_2$ | CH$_3$ | SO$_2$N(CH$_3$)$_2$ | CH$_3$ | — | CH$_3$ |
| J$_2$ | CH$_3$ | SO$_2$CH$_3$ | SO$_2$CH$_3$ | — | OCH$_3$ |
| J$_2$ | CH$_3$ | SO$_2$CH$_2$CH$_3$ | CH$_3$ | — | CH$_3$ |
| J$_7$ | — | CH$_3$ | — | SCH$_3$ | OCH$_3$ |
| J$_7$ | — | Cl | — | CH$_3$ | OCH$_3$ |
| J$_7$ | — | CO$_2$CH$_3$ | — | CH$_3$ | CH$_3$ |
| J$_7$ | — | H | — | SO$_2$CH$_3$ | OCH$_3$ |
| J$_7$ | — | SO$_2$CH$_3$ | — | Cl | OCH$_3$ |
| J$_7$ | — | SO$_2$N(CH$_3$)$_2$ | — | SCH$_3$ | CH$_3$ |
| J$_8$ | — | CH$_3$ | — | — | OCH$_3$ |
| J$_8$ | — | Cl | — | — | CH$_3$ |
| J$_8$ | — | CO$_2$CH$_3$ | — | — | OCH$_3$ |
| J$_8$ | — | CO$_2$CH$_2$CH$_3$ | — | — | OCH$_2$CH$_3$ |
| J$_8$ | — | NO$_2$ | — | — | CH$_3$ |
| J$_8$ | — | SO$_2$CH$_3$ | — | — | OCH$_3$ |
| J$_9$ | — | Cl | — | CH$_3$ | OCH$_3$ |
| J$_9$ | — | CO$_2$CH$_3$ | — | H | OCH$_3$ |
| J$_9$ | — | SO$_2$CH$_3$ | — | CH$_3$ | CH$_3$ |
| J$_{10}$ | — | Cl | — | CH$_3$ | OCH$_3$ |
| J$_{10}$ | — | CO$_2$CH$_3$ | — | SCH$_3$ | OCH$_3$ |
| J$_{10}$ | — | SO$_2$CH$_3$ | — | Cl | CH$_3$ |
| J$_{11}$ | — | Cl | — | — | OCH$_3$ |
| J$_{11}$ | — | CO$_2$CH$_3$ | — | — | OCH$_3$ |
| J$_{11}$ | — | SO$_2$N(CH$_3$)$_2$ | — | — | OCH$_3$ |
| J$_{11}$ | — | SO$_2$CH$_3$ | — | — | CH$_3$ |

TABLE XIII $$\underset{JSO_2NHCNHA_3}{\overset{O}{\parallel}}$$

| J | R$_9$ | R$_{10}$ | R$_{11}$ | R$_{12}$ | R$_{13}$ | R$_{14}$ | X$_1$ |
|---|---|---|---|---|---|---|---|
| J$_4$ | H | CO$_2$CH$_3$ | H | — | — | — | OCH$_3$ |
| J$_4$ | CH$_3$ | CO$_2$CH$_3$ | CH$_3$ | — | — | — | CH$_3$ |
| J$_4$ | CH$_3$ | CO$_2$CH$_2$CH$_3$ | H | — | — | — | OCH$_3$ |
| J$_4$ | CH$_3$ | SO$_2$N(CH$_3$)$_2$ | CH$_3$ | — | — | — | OCH$_2$CH$_3$ |
| J$_4$ | CH$_3$ | SO$_2$CH$_3$ | CH$_3$ | — | — | — | CH$_3$ |
| J$_4$ | CH$_3$ | SO$_2$CH$_3$ | CH$_3$ | — | — | — | OCF$_2$H |
| J$_4$ | CH$_2$CH$_2$CH$_2$ | CO$_2$CH$_3$ | CH$_3$ | — | — | — | OCH$_3$ |
| J$_4$ | CH$_3$ | NO$_2$ | CH$_3$ | — | — | — | OCH$_3$ |
| J$_4$ | CH$_3$ | SO$_2$CH$_2$CH$_3$ | H | — | — | — | CH$_3$ |

TABLE XIII-continued $$\text{JSO}_2\text{NHCNHA}_3$$
(with C=O)

| J | R$_9$ | R$_{10}$ | R$_{11}$ | R$_{12}$ | R$_{13}$ | R$_{14}$ | X$_1$ |
|---|---|---|---|---|---|---|---|
| J$_4$ | Ph | CO$_2$CH$_3$ | H | — | — | — | OCH$_3$ |
| J$_5$ | — | CO$_2$CH$_3$ | CH$_3$ | — | — | — | OCH$_3$ |
| J$_5$ | — | CO$_2$CH$_3$ | H | — | — | — | OCH$_3$ |
| J$_5$ | — | CO$_2$H$_3$ | H | — | — | — | CH$_3$ |
| J$_5$ | — | SO$_2$N(CH$_3$)$_2$ | H | — | — | — | OCH$_3$ |
| J$_5$ | — | SO$_2$N(CH$_3$)Et | H | — | — | — | OCH$_3$ |
| J$_5$ | — | SO$_2$CH$_3$ | CH$_3$ | — | — | — | CH$_3$ |
| J$_5$ | — | SO$_2$CH$_3$ | CH$_3$ | — | — | — | OCH$_3$ |
| J$_5$ | — | SO$_2$CH$_2$CH$_3$ | CH$_3$ | — | — | — | OCH$_3$ |
| J$_5$ | — | NO$_2$ | H | — | — | — | OCH$_3$ |
| J$_6$ | — | — | — | H | CO$_2$CH$_3$ | H | CH$_3$ |
| J$_6$ | — | — | — | H | CO$_2$CH$_3$ | CH$_3$ | OCH$_3$ |
| J$_6$ | — | — | — | CH$_3$ | H | CH$_3$ | CH$_3$ |
| J$_6$ | — | — | — | H | SO$_2$N(CH$_3$)$_2$ | CH$_3$ | OCH$_3$ |
| J$_6$ | — | — | — | NO$_2$ | H | CH$_3$ | OCH$_3$ |
| J$_6$ | — | — | — | H | SO$_2$CH$_3$ | CH$_3$ | OCH$_3$ |
| J$_6$ | — | — | — | CO$_2$CH$_3$ | H | CH$_3$ | CH$_3$ |
| J$_6$ | — | — | — | CO$_2$CH$_3$ | H | CH$_3$ | CH$_3$ |
| J$_6$ | — | — | — | SO$_2$CH$_3$ | H | CH$_3$ | OCH$_3$ |

TABLE XIV $$\text{JSO}_2\text{NHCNHA}_4$$
(with C=O)

| J | R$_1$ | R$_2$ | R$_3$ | R$_7$ | R$_8$ | X$_1$ | Y$_3$ |
|---|---|---|---|---|---|---|---|
| J$_1$ | CH$_3$ | H | H | — | — | CH$_3$ | H |
| J$_1$ | CH$_3$ | CH$_3$ | CH$_3$ | — | — | OCH$_3$ | H |
| J$_1$ | CO$_2$CH$_3$ | CH$_3$ | CH$_3$ | — | — | CH$_3$ | H |
| J$_1$ | CO$_2$CH$_3$ | H | H | — | — | OCH$_3$ | H |
| J$_1$ | CO$_2$CH$_3$ | H | H | — | — | OCF$_2$H | CH$_3$ |
| J$_1$ | CO$_2$CH$_3$ | CH$_3$ | H | — | — | OCH$_3$ | CH$_3$ |
| J$_1$ | CO$_2$CH$_2$CH$_3$ | H | H | — | — | CH$_3$ | CH$_3$ |
| J$_1$ | CO$_2$CH$_2$CH$_3$ | CH$_3$ | H | — | — | CH$_3$ | H |
| J$_1$ | SO$_2$N(CH$_3$)$_2$ | H | H | — | — | CH$_3$ | H |
| J$_1$ | SO$_2$N(CH$_3$)$_2$ | H | CH$_3$ | — | — | OCH$_3$ | H |
| J$_1$ | SO$_2$N(CH$_3$)$_2$ | CH$_3$ | CH$_3$ | — | — | OCH$_2$CH$_3$ | CH$_3$ |
| J$_1$ | SO$_2$N(CH$_2$CH$_3$)$_2$ | H | H | — | — | OCH$_3$ | CH$_3$ |
| J$_1$ | SO$_2$CH$_3$ | H | H | — | — | OCH$_3$ | CH$_3$ |
| J$_1$ | SO$_2$CH$_3$ | H | CH$_3$ | — | — | OCH$_3$ | H |
| J$_1$ | SO$_2$CH$_3$ | CH$_3$ | CH$_3$ | — | — | CH$_3$ | H |
| J$_1$ | SO$_2$CH$_2$CH$_3$ | CH$_3$ | CH$_3$ | — | — | CH$_3$ | H |
| J$_3$ | — | — | — | H | CO$_2$CH$_3$ | CH$_3$ | CH$_3$ |
| J$_3$ | — | — | — | H | CO$_2$CH$_2$CH$_3$ | CH$_3$ | CH$_3$ |
| J$_3$ | — | — | — | CH$_3$ | SO$_2$N(CH$_3$)$_2$ | OCH$_3$ | CH$_3$ |
| J$_3$ | — | — | — | CH$_3$ | SO$_2$N(OCH$_3$)CH$_3$ | OCH$_3$ | H |
| J$_3$ | — | — | — | H | SO$_2$CH$_3$ | OCH$_3$ | H |
| J$_3$ | — | — | — | CH$_3$ | SO$_2$CH$_3$ | OCH$_3$ | H |
| J$_3$ | — | — | — | CH$_3$ | SO$_2$CH$_3$ | CH$_3$ | CH$_3$ |
| J$_3$ | — | — | — | CH$_3$ | NO$_2$ | CH$_3$ | CH$_3$ |

TABLE XV $$\text{JSO}_2\text{NHCNHA}_4$$
(with C=O)

| J | R$_4$ | R$_5$ | R$_6$ | R$_{19}$ | X$_1$ | Y$_3$ |
|---|---|---|---|---|---|---|
| J$_2$ | H | CH$_3$ | CH$_3$ | — | CH$_3$ | H |
| J$_2$ | CH$_3$ | Cl | CH$_3$ | — | OCH$_3$ | H |
| J$_2$ | H | Br | CH$_2$CH$_2$CH$_3$ | — | OCH$_3$ | H |
| J$_2$ | CH$_3$ | CO$_2$CH$_3$ | CH$_3$ | — | OCH$_3$ | CH$_3$ |
| J$_2$ | CH$_3$ | SO$_2$N(CH$_3$)$_2$ | CH$_3$ | — | CH$_3$ | CH$_3$ |
| J$_2$ | CH$_3$ | H | SO$_2$CH$_3$ | — | OCH$_3$ | CH$_3$ |
| J$_2$ | CH$_3$ | SO$_2$CH$_2$CH$_3$ | CH$_3$ | — | CH$_3$ | H |
| J$_7$ | — | CH$_3$ | — | SCH$_3$ | OCH$_3$ | CH$_3$ |
| J$_7$ | — | Cl | — | CH$_3$ | OCH$_3$ | CH$_3$ |
| J$_7$ | — | CO$_2$CH$_3$ | — | CH$_3$ | CH$_3$ | CH$_3$ |
| J$_7$ | — | H | — | SO$_2$CH$_3$ | OCH$_3$ | CH$_3$ |
| J$_7$ | — | SO$_2$CH$_3$ | — | Cl | OCH$_3$ | CH$_3$ |
| J$_7$ | — | SO$_2$N(CH$_3$)$_2$ | — | SCH$_3$ | CH$_3$ | H |
| J$_8$ | — | CH$_3$ | — | — | OCH$_3$ | H |
| J$_8$ | — | Cl | — | — | CH$_3$ | H |

TABLE XV-continued $$JSO_2NHCNHA_4$$ (with C=O)

| J | R$_4$ | R$_5$ | R$_6$ | R$_{19}$ | X$_1$ | Y$_3$ |
|---|---|---|---|---|---|---|
| J$_8$ | — | CO$_2$CH$_3$ | — | — | OCH$_3$ | H |
| J$_8$ | — | CO$_2$CH$_2$CH$_3$ | — | — | OCH$_2$CH$_3$ | CH$_3$ |
| J$_8$ | — | NO$_2$ | — | — | CH$_3$ | CH$_3$ |
| J$_8$ | — | SO$_2$CH$_3$ | — | — | OCH$_3$ | CH$_3$ |
| J$_9$ | — | Cl | — | CH$_3$ | OCH$_3$ | H |
| J$_9$ | — | CO$_2$CH$_3$ | — | CH$_3$ | OCH$_3$ | H |
| J$_9$ | — | SO$_2$CH$_3$ | — | CH$_3$ | CH$_3$ | CH$_3$ |
| J$_{10}$ | — | Cl | — | CH$_3$ | OCH$_3$ | H |
| J$_{10}$ | — | CO$_2$CH$_3$ | — | SCH$_3$ | OCH$_3$ | CH$_3$ |
| J$_{10}$ | — | SO$_2$CH$_3$ | — | Cl | CH$_3$ | CH$_3$ |
| J$_{11}$ | — | Cl | — | — | OCF$_2$H | CH$_3$ |
| J$_{11}$ | — | CO$_2$CH$_3$ | — | — | OCH$_3$ | H |
| J$_{11}$ | — | SO$_2$N(CH$_3$)$_2$ | — | — | OCH$_3$ | H |
| J$_{11}$ | — | SO$_2$CH$_3$ | — | — | CH$_3$ | H |

TABLE XVI $$JSO_2NHCNHA_4$$ (with C=O)

| J | R$_9$ | R$_{10}$ | R$_{11}$ | R$_{12}$ | R$_{13}$ | R$_{14}$ | X$_1$ | Y$_3$ |
|---|---|---|---|---|---|---|---|---|
| J$_4$ | H | CO$_2$CH$_3$ | H | — | — | — | OCH$_3$ | H |
| J$_4$ | CH$_3$ | CO$_2$CH$_3$ | CH$_3$ | — | — | — | CH$_3$ | H |
| J$_4$ | CH$_3$ | CO$_2$CH$_2$CH$_3$ | H | — | — | — | OCH$_3$ | H |
| J$_4$ | CH$_3$ | SO$_2$N(CH$_3$)$_2$ | CH$_3$ | — | — | — | OCH$_3$ | H |
| J$_4$ | CH$_3$ | SO$_2$N(OCH$_3$)CH$_3$ | CH$_3$ | — | — | — | OCH$_2$CH$_3$ | CH$_3$ |
| J$_4$ | CH$_3$ | SO$_2$CH$_3$ | CH$_3$ | — | — | — | OCF$_2$H | CH$_3$ |
| J$_4$ | CH$_2$CH$_2$CH$_3$ | CO$_2$CH$_3$ | CH$_3$ | — | — | — | OCH$_3$ | CH$_3$ |
| J$_4$ | CH$_3$ | NO$_2$ | CH$_3$ | — | — | — | OCH$_3$ | CH$_3$ |
| J$_4$ | CH$_3$ | SO$_2$CH$_2$CH$_3$ | H | — | — | — | CH$_3$ | CH$_3$ |
| J$_4$ | Ph | CO$_2$CH$_3$ | H | — | — | — | OCH$_3$ | CH$_3$ |
| J$_5$ | — | CO$_2$CH$_3$ | H | — | — | — | OCH$_2$CH$_3$ | H |
| J$_5$ | — | CO$_2$CH$_3$ | H | — | — | — | OCH$_3$ | H |
| J$_5$ | — | CO$_2$CH$_3$ | H | — | — | — | CH$_3$ | H |
| J$_5$ | — | SO$_2$N(CH$_3$)$_2$ | H | — | — | — | OCH$_3$ | H |
| J$_5$ | — | SO$_2$N(CH$_3$)Et | H | — | — | — | OCH$_3$ | H |
| J$_5$ | — | SO$_2$CH$_3$ | CH$_3$ | — | — | — | CH$_3$ | H |
| J$_5$ | — | SO$_2$CH$_3$ | CH$_3$ | — | — | — | OCH$_3$ | H |
| J$_5$ | — | SO$_2$CH$_2$CH$_3$ | CH$_3$ | — | — | — | OCH$_3$ | CH$_3$ |
| J$_5$ | — | NO$_2$ | H | — | — | — | OCH$_3$ | CH$_3$ |
| J$_6$ | — | — | — | H | CO$_2$CH$_3$ | H | CH$_3$ | CH$_3$ |
| J$_6$ | — | — | — | H | CO$_2$CH$_3$ | CH$_3$ | OCH$_3$ | CH$_3$ |
| J$_6$ | — | — | — | CH$_3$ | H | CH$_3$ | CH$_3$ | CH$_3$ |
| J$_6$ | — | — | — | H | SO$_2$N(CH$_3$)$_2$ | CH$_3$ | OCH$_3$ | CH$_3$ |
| J$_6$ | — | — | — | NO$_2$ | H | CH$_3$ | OCH$_3$ | H |
| J$_6$ | — | — | — | H | SO$_2$CH$_3$ | CH$_3$ | OCH$_3$ | H |
| J$_6$ | — | — | — | CO$_2$CH$_3$ | H | H | CH$_3$ | H |
| J$_6$ | — | — | — | CO$_2$CH$_3$ | H | CH$_3$ | CH$_3$ | H |
| J$_6$ | — | — | — | SO$_2$CH$_3$ | CH$_3$ | CH$_3$ | OCH$_3$ | H |

TABLE XVII $$JSO_2NHCNHA_5$$ (with C=O)

| J | R$_4$ | R$_5$ | R$_6$ | R$_{19}$ | X$_2$ | Y$_2$ |
|---|---|---|---|---|---|---|
| J$_2$ | H | CH$_3$ | CH$_3$ | — | CH$_3$ | OCH$_3$ |
| J$_2$ | CH$_3$ | Cl | CH$_3$ | — | CH$_3$ | OCH$_3$ |
| J$_2$ | H | Br | CH$_2$CH$_2$CH$_3$ | — | CH$_3$ | OCH$_3$ |
| J$_2$ | CH$_3$ | CO$_2$CH$_3$ | CH$_3$ | — | CH$_3$ | OCH$_3$ |
| J$_2$ | CH$_3$ | SO$_2$N(CH$_3$)$_2$ | CH$_3$ | — | CH$_3$ | OCH$_3$ |
| J$_2$ | CH$_3$ | H | SO$_2$CH$_3$ | — | CH$_3$ | CH$_3$ |
| J$_2$ | CH$_3$ | SO$_2$CH$_2$CH$_3$ | CH$_3$ | — | C$_2$H$_5$ | OCH$_2$CH$_3$ |
| J$_7$ | — | CH$_3$ | — | SCH$_3$ | CH$_2$CF$_3$ | OCH$_3$ |
| J$_7$ | — | Cl | — | CH$_3$ | CH$_3$ | OCH$_3$ |
| J$_7$ | — | CO$_2$CH$_3$ | — | CH$_3$ | CH$_3$ | OCH$_3$ |
| J$_7$ | — | H | — | SO$_2$CH$_3$ | CH$_3$ | OCH$_3$ |
| J$_7$ | — | SO$_2$CH$_3$ | — | Cl | CH$_3$ | SCH$_3$ |
| J$_7$ | — | SO$_2$N(CH$_3$)$_2$ | — | SCH$_3$ | C$_2$H$_5$ | OCH$_3$ |
| J$_8$ | — | CH$_3$ | — | — | CH$_2$CF$_3$ | OCH$_3$ |
| J$_8$ | — | Cl | — | — | CH$_3$ | OCH$_3$ |
| J$_8$ | — | CO$_2$CH$_3$ | — | — | CH$_3$ | SCF$_2$H |

TABLE XVII-continued $$\underset{\text{JSO}_2\text{NHCNHA}_5}{\overset{\overset{\text{O}}{\|}}{}}$$

| J | $R_4$ | $R_5$ | $R_6$ | $R_{19}$ | $X_2$ | $Y_2$ |
|---|---|---|---|---|---|---|
| $J_8$ | — | $CO_2CH_2CH_3$ | — | — | $CH_3$ | $OCH_3$ |
| $J_8$ | — | $NO_2$ | — | — | $CH_3$ | $OCH_3$ |
| $J_8$ | — | $SO_2CH_3$ | — | — | $CH_2CH_3$ | $OCH_3$ |
| $J_9$ | — | Cl | — | $CH_3$ | $CH_3$ | $OCH_3$ |
| $J_9$ | — | $CO_2CH_3$ | — | $SO_2CH_3$ | $CH_3$ | $CH_3$ |
| $J_9$ | — | $SO_2CH_3$ | — | $CH_3$ | $CH_3$ | $OCH_3$ |
| $J_{10}$ | — | Cl | — | $CH_3$ | $CH_3$ | $SCH_2CH_3$ |
| $J_{10}$ | — | $CO_2CH_3$ | — | $SCH_3$ | $C_2H_5$ | $OCH_3$ |
| $J_{10}$ | — | $SO_2CH_3$ | — | Cl | $CH_2CF_3$ | $OCH_3$ |
| $J_{11}$ | — | Cl | — | — | $CH_3$ | $OCH_3$ |
| $J_{11}$ | — | $CO_2CH_3$ | — | — | $CH_3$ | $SC_2H_5$ |
| $J_{11}$ | — | $SO_2N(CH_3)_2$ | — | — | $CH_3$ | $OCH_3$ |
| $J_{11}$ | — | $SO_2CH_3$ | — | — | $CH_3$ | $OCH_3$ |

TABLE XVIII $$\underset{\text{JSO}_2\text{NHCNHA}_5}{\overset{\overset{\text{O}}{\|}}{}}$$

| J | $R_1$ | $R_2$ | $R_3$ | $R_7$ | $R_8$ | $X_2$ | $Y_2$ |
|---|---|---|---|---|---|---|---|
| $J_1$ | $CH_3$ | H | H | — | — | $CH_3$ | $OCH_3$ |
| $J_1$ | $CH_3$ | $CH_3$ | $CH_3$ | — | — | $CH_3$ | $OCH_3$ |
| $J_1$ | $CO_2CH_3$ | $CH_3$ | $CH_3$ | — | — | $CH_3$ | $OCH_3$ |
| $J_1$ | $CO_2CH_3$ | H | H | — | — | $CH_3$ | $OCH_3$ |
| $J_1$ | $CO_2CH_3$ | H | H | — | — | $CH_3$ | $OCH_3$ |
| $J_1$ | $CO_2CH_3$ | $CH_3$ | H | — | — | $C_2H_5$ | $OCH_3$ |
| $J_1$ | $CO_2CH_2CH_3$ | H | H | — | — | $CH_2CF_3$ | $OCH_3$ |
| $J_1$ | $CO_2CH_2CH_3$ | $CH_3$ | H | — | — | $CH_3$ | $OCH_3$ |
| $J_1$ | $SO_2N(CH_3)_2$ | H | H | — | — | $CH_3$ | $CH_3$ |
| $J_1$ | $SO_2N(CH_3)_2$ | H | $CH_3$ | — | — | $CH_3$ | OEt |
| $J_1$ | $SO_2N(CH_3)_2$ | $CH_3$ | $CH_3$ | — | — | $CH_3$ | $OCH_3$ |
| $J_1$ | $SO_2N(CH_2CH_3)_2$ | H | H | — | — | $CH_3$ | $OCH_3$ |
| $J_1$ | $SO_2CH_3$ | H | H | — | — | $CH_3$ | $OCH_3$ |
| $J_1$ | $SO_2CH_3$ | H | $CH_3$ | — | — | $CH_3$ | $SCH_3$ |
| $J_1$ | $SO_2CH_3$ | $CH_3$ | $CH_3$ | — | — | $CH_3$ | $CH_2CH_3$ |
| $J_1$ | $SO_2CH_2CH_3$ | $CH_3$ | $CH_3$ | — | — | $C_2H_5$ | $OCH_3$ |
| $J_3$ | — | — | — | H | $CO_2CH_3$ | $CH_2CF_3$ | $OCH_3$ |
| $J_3$ | — | — | — | H | $CO_2CH_2CH_3$ | $CH_3$ | $OCH_3$ |
| $J_3$ | — | — | — | $CH_3$ | $SO_2N(CH_3)_2$ | $CH_3$ | $SCF_2H$ |
| $J_3$ | — | — | — | $CH_3$ | $SO_2N(OCH_3)CH_3$ | $CH_3$ | $OCH_3$ |
| $J_3$ | — | — | — | H | $SO_2CH_3$ | $CH_3$ | $OCH_3$ |
| $J_3$ | — | — | — | H | $SO_2CH_3$ | $CH_3$ | $OCH_3$ |
| $J_3$ | — | — | — | $CH_3$ | $SO_2CH_2CH_3$ | $CH_3$ | $SCH_2CH_3$ |
| $J_3$ | — | — | — | $CH_3$ | $NO_2$ | $CH_3$ | $OCH_3$ |

TABLE XIX $$\underset{\text{JSO}_2\text{NHCNHA}_5}{\overset{\overset{\text{O}}{\|}}{}}$$

| J | $R_9$ | $R_{10}$ | $R_{11}$ | $R_{12}$ | $R_{13}$ | $R_{14}$ | $X_2$ | $Y_2$ |
|---|---|---|---|---|---|---|---|---|
| $J_4$ | H | $CO_2CH_3$ | H | — | — | — | $CH_3$ | $OCH_3$ |
| $J_4$ | $CH_3$ | $CO_2CH_3$ | $CH_3$ | — | — | — | $CH_3$ | $OCH_3$ |
| $J_4$ | $CH_3$ | $CO_2CH_2CH_3$ | H | — | — | — | $CH_3$ | $OCH_3$ |
| $J_4$ | $CH_3$ | $SO_2N(CH_3)_2$ | $CH_3$ | — | — | — | $CH_3$ | $OCH_3$ |
| $J_4$ | $CH_3$ | $SO_2N(OCH_3)CH_3$ | $CH_3$ | — | — | — | $CH_3$ | $OCH_3$ |
| $J_4$ | $CH_3$ | $SO_2CH_3$ | $CH_3$ | — | — | — | $C_2H_5$ | $OCH_3$ |
| $J_4$ | $CH_3$ | $SO_2CH_3$ | $CH_3$ | — | — | — | $CH_3$ | $OCH_3$ |
| $J_4$ | $CH_2CH_2CH_3$ | $CO_2CH_3$ | $CH_3$ | — | — | — | $CH_3$ | $CH_3$ |
| $J_4$ | $CH_3$ | $NO_2$ | $CH_3$ | — | — | — | $OCH_3$ | $OCH_2CH_3$ |
| $J_4$ | $CH_3$ | $SO_2CH_2CH_3$ | H | — | — | — | $CH_3$ | $OCH_3$ |
| $J_4$ | Ph | $CO_2CH_3$ | H | — | — | — | $CH_2CF_3$ | $CH_3$ |
| $J_5$ | — | $CO_2CH_3$ | H | — | — | — | $CH_3$ | $OCH_3$ |
| $J_5$ | — | $CO_2CH_3$ | H | — | — | — | $CH_3$ | $CH_2CH_3$ |
| $J_5$ | — | $CO_2CH_3$ | H | — | — | — | $CH_3$ | $OCH_3$ |
| $J_5$ | — | $SO_2N(CH_3)_2$ | H | — | — | — | $CH_3$ | $OCH_3$ |
| $J_5$ | — | $SO_2N(CH_3)Et$ | H | — | — | — | $CH_3$ | $SCHF_2$ |
| $J_5$ | — | $SO_2CH_3$ | $CH_3$ | — | — | — | $CH_3$ | $OCH_3$ |
| $J_5$ | — | $SO_2CH_3$ | $CH_3$ | — | — | — | $CH_2CH_3$ | $OCH_3$ |
| $J_5$ | — | $SO_2CH_2CH_3$ | $CH_3$ | — | — | — | $CH_3$ | $OCH_3$ |
| $J_5$ | — | $NO_2$ | H | — | — | — | $CH_3$ | $OCH_3$ |
| $J_6$ | — | — | — | H | $CO_2CH_3$ | H | $CH_3$ | $SCH_2CH_3$ |

TABLE XIX-continued $$JSO_2NHCNHA_5$$ (with C=O)

| J | $R_9$ | $R_{10}$ | $R_{11}$ | $R_{12}$ | $R_{13}$ | $R_{14}$ | $X_2$ | $Y_2$ |
|---|---|---|---|---|---|---|---|---|
| $J_6$ | — | — | — | H | $CO_2CH_3$ | $CH_3$ | $CH_3$ | $OCH_3$ |
| $J_6$ | — | — | — | $CH_3$ | $CO_2CH_3$ | $CH_3$ | $CH_3$ | $OCH_3$ |
| $J_6$ | — | — | — | H | $SO_2N(CH_3)_2$ | $CH_3$ | $CH_3$ | $OCH_3$ |
| $J_6$ | — | — | — | $CH_3$ | $SO_2N(CH_3)_2$ | $CH_3$ | $CH_3$ | $OCH_3$ |
| $J_6$ | — | — | — | H | $SO_2CH_3$ | $CH_3$ | $CH_2CF_3$ | $OCH_3$ |
| $J_6$ | — | — | — | $CO_2CH_3$ | H | H | $CH_3$ | $OCH_3$ |
| $J_6$ | — | — | — | $CO_2CH_3$ | H | $CH_3$ | $CH_3$ | $OCH_3$ |
| $J_6$ | — | — | — | $SO_2CH_3$ | $CH_3$ | $CH_3$ | $CH_3$ | $OCH_3$ |

TABLE XX $$JSO_2NHCNHA_6$$ (with C=O)

| J | $R_9$ | $R_{10}$ | $R_{11}$ | $R_{12}$ | $R_{13}$ | $R_{14}$ | $X_3$ |
|---|---|---|---|---|---|---|---|
| $J_4$ | H | $CO_2CH_3$ | H | — | — | — | $CH_3$ |
| $J_4$ | $CH_3$ | $CO_2CH_3$ | $CH_3$ | — | — | — | $OCH_3$ |
| $J_4$ | $CH_3$ | $CO_2CH_2CH_3$ | H | — | — | — | $CH_3$ |
| $J_4$ | $CH_3$ | $SO_2N(CH_3)_2$ | $CH_3$ | — | — | — | $OCH_3$ |
| $J_4$ | $CH_3$ | $SO_2N(OCH_3)CH_3$ | $CH_3$ | — | — | — | $CH_3$ |
| $J_4$ | $CH_3$ | $SO_2CH_3$ | $CH_3$ | — | — | — | $OCH_3$ |
| $J_4$ | $CH_3$ | $SO_2CH_3$ | $CH_3$ | — | — | — | $CH_3$ |
| $J_4$ | $CH_2CH_2CH_3$ | $CO_2CH_3$ | $CH_3$ | — | — | — | $OCH_3$ |
| $J_4$ | $CH_3$ | $NO_2$ | $CH_3$ | — | — | — | $CH_3$ |
| $J_4$ | $CH_3$ | $SO_2CH_2CH_3$ | H | — | — | — | $OCH_3$ |
| $J_4$ | Ph | $CO_2CH_3$ | H | — | — | — | $CH_3$ |
| $J_5$ | — | $CO_2CH_3$ | H | — | — | — | $OCH_3$ |
| $J_5$ | — | $CO_2CH_3$ | H | — | — | — | $CH_3$ |
| $J_5$ | — | $CO_2CH_3$ | $CH_3$ | — | — | — | $OCH_3$ |
| $J_5$ | — | $SO_2N(CH_3)_2$ | H | — | — | — | $CH_3$ |
| $J_5$ | — | $SO_2N(CH_3)Et$ | H | — | — | — | $OCH_3$ |
| $J_5$ | — | $SO_2CH_3$ | $CH_3$ | — | — | — | $CH_3$ |
| $J_5$ | — | $SO_2CH_3$ | $CH_3$ | — | — | — | $OCH_3$ |
| $J_5$ | — | $SO_2CH_2CH_3$ | $CH_3$ | — | — | — | $CH_3$ |
| $J_5$ | — | $NO_2$ | H | — | — | — | $OCH_3$ |
| $J_6$ | — | — | — | H | $CO_2CH_3$ | H | $CH_3$ |
| $J_6$ | — | — | — | H | $CO_2CH_3$ | $CH_3$ | $OCH_3$ |
| $J_6$ | — | — | — | $CH_3$ | H | $CH_3$ | $CH_3$ |
| $J_6$ | — | — | — | H | $SO_2N(CH_3)_2$ | $CH_3$ | $OCH_3$ |
| $J_6$ | — | — | — | $NO_2$ | H | $CH_3$ | $CH_3$ |
| $J_6$ | — | — | — | H | $SO_2CH_3$ | $CH_3$ | $OCH_3$ |
| $J_6$ | — | — | — | $CO_2CH_3$ | H | H | $CH_3$ |
| $J_6$ | — | — | — | $CO_2CH_3$ | H | $CH_3$ | $OCH_3$ |
| $J_6$ | — | — | — | $SO_2CH_3$ | $CH_3$ | $CH_3$ | $CH_3$ |

TABLE XXI $$JSO_2NHCNHA_6$$ (with C=O)

| J | $R_1$ | $R_2$ | $R_3$ | $R_7$ | $R_8$ | $X_3$ |
|---|---|---|---|---|---|---|
| $J_1$ | $CH_3$ | H | H | — | — | $CH_3$ |
| $J_1$ | $CH_3$ | $CH_3$ | $CH_3$ | — | — | $OCH_3$ |
| $J_1$ | $CO_2CH_3$ | $CH_3$ | $CH_3$ | — | — | $CH_3$ |
| $J_1$ | $CO_2CH_3$ | H | H | — | — | $OCH_3$ |
| $J_1$ | $CO_2CH_3$ | H | H | — | — | $CH_3$ |
| $J_1$ | $CO_2CH_3$ | $CH_3$ | $CH_3$ | — | — | $OCH_3$ |
| $J_1$ | $CO_2CH_2CH_3$ | H | H | — | — | $CH_3$ |
| $J_1$ | $CO_2CH_2CH_3$ | $CH_3$ | H | — | — | $CH_3$ |
| $J_1$ | $SO_2N(CH_3)_2$ | H | H | — | — | $OCH_3$ |
| $J_1$ | $SO_2N(CH_3)_2$ | $CH_3$ | H | — | — | $CH_3$ |
| $J_1$ | $SO_2N(CH_3)_2$ | $CH_3$ | $CH_3$ | — | — | $OCH_3$ |
| $J_1$ | $SO_2N(CH_2CH_3)_2$ | H | H | — | — | $CH_3$ |
| $J_1$ | $SO_2CH_3$ | H | H | — | — | $OCH_3$ |
| $J_1$ | $SO_2CH_3$ | H | $CH_3$ | — | — | $CH_3$ |
| $J_1$ | $SO_2CH_3$ | $CH_3$ | $CH_3$ | — | — | $OCH_3$ |
| $J_1$ | $SO_2CH_2CH_3$ | $CH_3$ | $CH_3$ | — | — | $OCH_3$ |
| $J_3$ | — | — | — | H | $CO_2CH_3$ | $CH_3$ |
| $J_3$ | — | — | — | H | $CO_2CH_3$ | $OCH_3$ |
| $J_3$ | — | — | — | $CH_3$ | $SO_2N(CH_3)_2$ | $CH_3$ |
| $J_3$ | — | — | — | $CH_3$ | $SO_2N(OCH_3)CH_3$ | $OCH_3$ |
| $J_3$ | — | — | — | H | $SO_2CH_3$ | $CH_3$ |
| $J_3$ | — | — | — | H | $SO_2CH_3$ | $OCH_3$ |
| $J_3$ | — | — | — | $CH_3$ | $SO_2CH_3$ | $CH_3$ |
| $J_3$ | — | — | — | $CH_3$ | $NO_2$ | $OCH_3$ |

TABLE XXII $$JSO_2NHCNHA_6$$ (with C=O)

| J | $R_4$ | $R_5$ | $R_6$ | $R_{19}$ | $X_3$ |
|---|---|---|---|---|---|
| $J_2$ | H | $CH_3$ | $CH_3$ | — | $CH_3$ |
| $J_2$ | $CH_3$ | Cl | $CH_3$ | — | $OCH_3$ |
| $J_2$ | H | Br | $CH_2CH_2CH_3$ | — | $CH_3$ |
| $J_2$ | $CH_3$ | $CO_2CH_3$ | $CH_3$ | — | $OCH_3$ |
| $J_2$ | $CH_3$ | $SO_2N(CH_3)_2$ | $CH_3$ | — | $CH_3$ |
| $J_2$ | $CH_3$ | H | $SO_2CH_3$ | — | $OCH_3$ |
| $J_2$ | $CH_3$ | $SO_2CH_2CH_3$ | $CH_3$ | — | $CH_3$ |
| $J_7$ | — | $CH_3$ | — | $SCH_3$ | $OCH_3$ |
| $J_7$ | — | Cl | — | $CH_3$ | $CH_3$ |

TABLE XXII-continued $$JSO_2NHCNHA_6$$ (with C=O)

| J | R$_4$ | R$_5$ | R$_6$ | R$_{19}$ | X$_3$ |
|---|---|---|---|---|---|
| J$_7$ | — | CO$_2$CH$_3$ | — | CH$_3$ | OCH$_3$ |
| J$_7$ | — | H | — | SO$_2$CH$_3$ | CH$_3$ |
| J$_7$ | — | SO$_2$CH$_3$ | — | Cl | OCH$_3$ |
| J$_7$ | — | SO$_2$N(CH$_3$)$_2$ | — | SCH$_3$ | CH$_3$ |
| J$_8$ | — | CH$_3$ | — | — | OCH$_3$ |
| J$_8$ | — | Cl | — | — | CH$_3$ |
| J$_8$ | — | CO$_2$CH$_3$ | — | — | OCH$_3$ |
| J$_8$ | — | CO$_2$CH$_2$CH$_3$ | — | — | CH$_3$ |
| J$_8$ | — | NO$_2$ | — | — | OCH$_3$ |
| J$_8$ | — | SO$_2$CH$_3$ | — | — | CH$_3$ |
| J$_9$ | — | Cl | — | CH$_3$ | OCH$_3$ |
| J$_9$ | — | CO$_2$CH$_3$ | — | CH$_3$ | CH$_3$ |
| J$_9$ | — | SO$_2$CH$_3$ | — | CH$_3$ | OCH$_3$ |
| J$_{10}$ | — | Cl | — | CH$_3$ | CH$_3$ |
| J$_{10}$ | — | CO$_2$CH$_3$ | — | SCH$_3$ | OCH$_3$ |
| J$_{10}$ | — | SO$_2$CH$_3$ | — | Cl | CH$_3$ |
| J$_{11}$ | — | Cl | — | — | OCH$_3$ |
| J$_{11}$ | — | CO$_2$CH$_3$ | — | — | CH$_3$ |
| J$_{11}$ | — | SO$_2$N(CH$_3$)$_2$ | — | — | OCH$_3$ |
| J$_{11}$ | — | SO$_2$CH$_3$ | — | — | CH$_3$ |

Formulations

Useful formulation of the compounds of Formula I can be prepared in conventional ways. They include wettable powers, dusts, suspensions, granules, pellets, solutions, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

TABLE XXIII

| | Percent by Weight | | |
|---|---|---|---|
| | Active Ingredient | Diluent(s) | Surfactant(s) |
| Wettable Powders | 20-90 | 0-74 | 1-10 |
| Oil Suspensions, Emulsions, Solutions, (including Emulsifiable Concentrates) | 5-50 | 40-95 | 0-15 |
| Aqueous Suspension | 10-50 | 40-84 | 1-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredients can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. Typical liquid diluents and solvents are described in Marsden, "Solvents Guide", 2nd. Ed., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 4th. Edn., McGraw-Hill, N.Y., 1963, pp. 8-59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5, Line 43 through Col. 7, Line 62 and Ex. 8, 12, 15, 39, 41, 52, 53, 58, 132, 138-140, 162-164, 166, 167, 169-182.

H. Gysin and E. Knusli, U.S. Pat. No. 2,891,855, June 23, 1959, Col. 3, Line 66 through Col. 5, Line 17 and Examples 1-4.

G. C. Klingman, "Weed Control as a Science", John Wiley & Sons, Inc., New York, 1961 pp. 81-96.

J. D. Fryer and S. A. Evans, "Weed Control Handbook", 5th Edn., Blackwell Scientific Publications, Oxford, 1968, pp. 101-103.

J. B. Buchanan, U.S. Pat. No. 3,576,834, Apr. 27, 1971, Col. 5, Line 36 through Col. 7, Line 70 and Ex. 1-4, 17, 106, 123-140.

R. R. Shaffer, U.S. Pat. No. 3,560,616 Feb. 2, 1971, Col. 3, Line 48 through Col. 7, Line 26 and Examples 3-9, 11-18.

E. Somers, "Formulation", Chapter 6 in Torgeson, "Fungicides", Vol. I, Academic Press, New York, 1967.

In the following examples, all parts are by weight unless otherwise indicated.

EXAMPLE 5

Wettable Powder

5-[[(4,6-dimethoxyprimidin-2-yl)aminocarbonyl-]aminosulfonylmethyl]-1,3-dimethyl-1H-pyrazole-4-carboxylic acid, ethyl ester: 80%
sodium alkylnaphthalenesulfonate: 2%
sodium ligninsulfonate: 2%
synthetic amorphous silica: 3%
kaolinite: 13%

The ingredients are thoroughly blended, passed through a mill, such as an air mill or hammer mill, to produce an average particle size under 25 microns, reblended and sifted through a U.S.S. No. 50 sieve (0.3 mm opening) before packaging.

EXAMPLE 6

Wettable Powder

3-[[(4,6-dimethoxypyrimidin-2-yl)aminocarbonyl-]aminosulfonylmethyl]-1,5-dimethyl-1H-pyrazole-4-carboxylic acid, ethyl ester: 20%
dioctyl sodium sulfosuccinate: 1.5%
sodium ligninsulfonate: 3%
low viscosity methyl cellulose: 1.5%
attapulgite: 74%

The ingredients are thoroughly blended, passed through an air or hammer mill to produce an average particle size under 25 microns, reblended and sifted through a U.S.S. No. 50 sieve (0.3 mm opening) before packaging.

EXAMPLE 7

High Strength Concentrate

3-[[(4,6-dimethoxypyrimidin-2-yl)aminocarbonyl-]aminosulfonylmethyl]-1,5-dimethyl-1H-pyrazole-4-carboxylic acid, ethyl ester: 98.5%
silica aerogel: 0.5%
synthetic amorphous fine silica: 1.0%

The ingredients are blended and ground in a hammer mill to produce a high strength concentrate essentially all passing a U.S.S. No. 50 sieve (0.3 mm openings). This material may then be formulated in a variety of ways.

EXAMPLE 8

Dust wettable powder of Example 6: 5%
pyrophyllite (powder): 95%

The wettable powder and the pyrophyllite diluent are thoroughly blended and then packaged. The product is suitable for use as a dust.

EXAMPLE 9

Dust

5-[[(4,6-dimethoxypyrimidin-2-yl)aminocarbonyl-]aminosulfonylmethyl]-1,3-dimethyl-1H-pyrazole-4-carboxylic acid, ethyl ester: 25%
attapulgite: 25%
talc: 50%

The active ingredient is blended with attapulgite and then passed through a hammer mill to produce particles substantially all below 200 microns. The ground concentrate is then blended with powdered talc until homogeneous.

EXAMPLE 10

Aqueous Suspension

5-[[(4,6-dimethoxypyrimidin-2-yl)aminocarbonyl-]aminosulfonylmethyl]-1,3-dimethyl-1H-pyrazole-4-carboxylic acid, ethyl ester: 25%
hydrated attapulgite: 3%
crude calcium ligninsulfonate: 10%
water: 62%

The ingredients are ground together in a ball, sand or roller mill until the solid particles have been reduced to diameters under 10 microns.

EXAMPLE 11

Aqueous Suspension

3-[[(4,6-dimethoxypyrimidin-2-yl)aminocarbonyl-]aminosulfonylmethyl]-1,5-dimethyl-1H-pyrazole-4-carboxylic acid, ethyl ester: 50.0%
dodecylphenol polyethylene glycol ether: 0.5%
crude calcium ligninsulfonate: 5.0%
xanthan gum thickener: 0.2%
paraformaldehyde: 0.2%
water: 44.1%

The ingredients are ground together in a sand, ball or roller mill to produce particles essentially all under five microns in size.

EXAMPLE 12

Oil Suspension

5-[[(4,6-dimethoxypyrimidin-2-yl)aminocarbonyl-]aminosulfonylmethyl]-1,3-dimethyl-1H-pyrazole-4-carboxylic acid, ethyl ester: 50%
blend of polyalcohol carboxylic esters and oil soluble petroleum sulfonates: 6%
xylene: 44%

The ingredients are combined and ground together in a sand, ball or roller mill to produce particles essentially all below 3 microns. The product can be used directly, extended with oils, or emulsified in water.

EXAMPLE 13

Oil suspension

3-[[(4,6-dimethoxypryimidin-2-yl)aminocarbonyl-]aminosulfonylmethyl]-1,5-dimethyl-1H-pyrazole-4-carboxylic acid, ethyl ester: 10%
polyoxyethylene sorbitol hexaoleate: 5%
highly aliphatic hydrocarbon oil: 85%

The ingredients are ground together in a sand mill until the solid particles have been reduced to under about 5 microns. The resulting thick suspension may be applied directly, but preferably after being extended with oils or emulsified in water.

EXAMPLE 14

Granule wettable powder of Example 6: 5%
attapulgite granules (U.S.S. #20-40; 0.84-0.42 mm): 95%

A slurry of wettable powder in water is sprayed on the surface of attapulgite granules in a double-cone blender. The granules are dried and packaged.

EXAMPLE 15

Granule wettable powder of Example 5: 94%
gypsum: 6%

The ingredients are blended in a rotating or fluid bed mixer and sprayed with water to accomplish granulation. When most of the material has reached the desired range of 2.0 to 0.25 mm. (U.S.S. #10 to 60 sieve), the granules are removed, dried, and screened. Oversize material is crushed to produce additional material in the desired range. These granules contain 75% active ingredient.

EXAMPLE 16

Extruded Pellet

3-[[(4,6-dimethoxypyrimidin-2-yl)aminocarbonyl-]aminosulfonylmethyl]-1,5-dimethyl-1H-pyrazole-4-carboxylic acid, ethyl ester: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer milled and then moistened with about 12% water. The mixture is extruded as cylinders about 1–3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 17

Solution

5-[[(4,6-dimethoxypyrimidin-2-yl)aminocarbonyl-]aminosulfonylmethyl]-1,3-dimethyl-1H-pyrazole-4-carboxylic acid, ethyl ester: 5%
dimethylformamide: 95%

The ingredients are combined and stirred to produce a solution, which can be used for low volume applications.

All compounds of the invention may be formulated in the same manner.

UTILITY

The compounds of the present invention are active herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, some of the subject compounds are useful for the selective control of weeds in wheat, rice or cotton and for plant growth modification, such as growth retardation.

The rates of application for the compounds of the invention are determined by a number of factors, including their use as plant growth modifiers or general herbicides, the crop species involved, the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, or for situations where only shortterm persistence is required.

The compounds of the invention may be used in combination with any other commercial herbicide; examples of which are those of the triazine, triazole, uracil, urea, amide, diphenylether, carbamate and bipyridylium types and mefluidide.

The herbicidal and plant growth modifying properties of the subject compounds were discovered in greenhouse tests. The test procedures and results follow.

Test A

Seeds of crabgrass (Digitaria sp.), barnyardgrass (Echinochloa crusgalli), wild oats (Avena fatua), sicklepod (Cassia obtusifolia), morningglory (Ipomoea sp.), cocklebur (Xanthium pensylvanicum), sorghum, corn, soybean, sugar beet, rice, wheat, cotton and purple nutsedge (Cyperus rotundus) tubers were planted and treated pre-emergence with the test chemicals dissolved in a non-phytotoxic solvent. At the same time, these crop and weed species were treated post-emergence with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from O=no injury, to 10=complete kill. The accompanying descriptive symbols have the following meanings:

C=chlorosis or necrosis;
E=emergence inhibition;
G=growth retardation; and
H=formative effects.

The data indicate that at the low rates of application selected for these evaluations, the compounds tested are active herbicides. Additionally, they often possess plant growth modifying properties, such as causing growth retardation.

Compounds

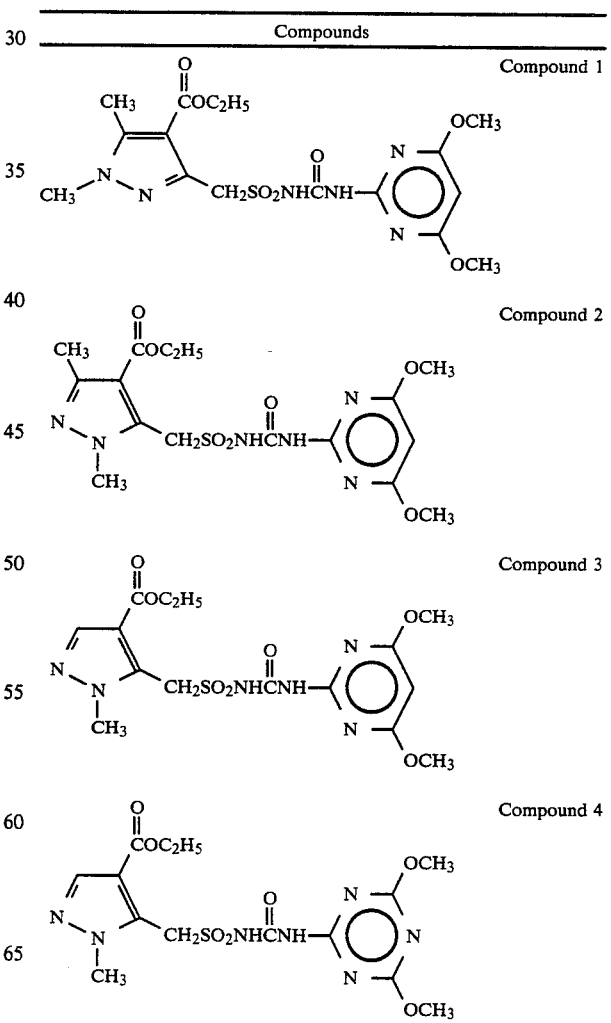

-continued

Compounds

Compound 5

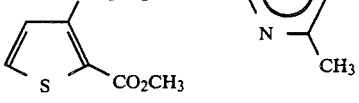

Compound 6

Compound 7

Compound 8

Compound 9

Compound 10

-continued

Compounds

Compound 11

Compound 12

Compound 13

Compound 14

Compound 15

Compound 16

TABLE A

| | Compound 1 | | | Compound 2 | | | Compound 3 | | Compound 4 | | Cmpd. 5 | | Cmpd. 6 | Cmpd. 7 |
|---|---|---|---|---|---|---|---|---|---|---|---|---|---|---|
| Rate kg/ha | 2.0 | 0.4 | 0.05 | 2.0 | 0.4 | 0.05 | 0.4 | 0.05 | 0.4 | 0.05 | 0.4 | 2.0 | 0.4 | 0.4 |
| POST-EMERGENCE | | | | | | | | | | | | | | |
| Morningglory | 5C,9G | 2C,8G | 4G | 9C | 9C | 9C | 4C,9G | 3C,6H | 2C,2H | 2H | 0 | 0 | 5C,8H | 2C,3H |
| Cocklebur | 2C,8G | 1C | 0 | 3H | 5G | 1H | 2C,5H | 0 | 0 | 0 | 0 | 0 | 0 | 3G |
| Sicklepod | 2C,9H | 3C,7H | 3C,5G | 5C,6G | 3C,4H | 4C,4H | 3C,8H | 3C,3H | 0 | 0 | 0 | — | 0 | 0 |
| Nutsedge | 8G | 5G | 7G | 8G | 8G | 8G | 3G | 4G | 0 | 0 | 0 | 0 | 0 | 0 |
| Crabgrass | 6G | 2G | 0 | 4G | 2G | 0 | 1C | 0 | 0 | 0 | 0 | 0 | 0 | 0 |
| Barnyardgrass | 3C,8H | 3C,8H | 2C,5H | 5C,9H | 3C,9H | 2C,3H | 0 | 0 | 0 | 0 | 0 | 0 | 2C,4H | 2C,5H |

TABLE A-continued

| | | | | | | | | | | | | | | |
|---|---|---|---|---|---|---|---|---|---|---|---|---|---|---|
| Wild Oats | 2C,5G | 0 | 0 | 2G | 0 | 0 | 0 | 0 | 0 | 0 | 0 | 0 | 0 | 0 |
| Wheat | 4G | 0 | 0 | 0 | 0 | 0 | 0 | 0 | 0 | 0 | 0 | 0 | 3G | 0 |
| Corn | 2C,9G | 3C,8G | 3C,8H | 2C,8H | 3C,8H | 2C,5H | 0 | 0 | 0 | 0 | 0 | 0 | 3C,8H | 2C,5H |
| Soybean | 3C,9H | 4C,8H | 3C,9G | 4C,8H | 5C,9G | 3C,7G | 2C,8G | 2C,2H | 0 | 0 | 0 | 0 | 2C,3H | 2C,3H |
| Rice | 2G | 2G | 0 | 2C,7G | 2C,7G | 4G | 0 | 0 | 0 | 0 | 0 | 0 | 4C,8G | 2C,6G |
| Sorghum | 3C,8H | 3C,8H | 3C,8H | 3C,8H | 3C,7G | 5G | 3C,5G | 2G | 0 | 0 | 0 | 0 | 5C,9H | 3C,5H |
| Sugar beet | 3C,7G | 3C,5G | 3G | 3C,8H | 1C,4G | 4G | 3C,6G | 2C,3G | 1C,1H | 0 | 0 | 0 | 4C,8H | 3C,6H |
| Cotton | 3C,9G | 4C,7G | 3C,5H | 4C,8G | 3C,8G | 2C,7G | 3C,8H | 0 | 0 | 0 | 0 | 0 | 4G | 2H |
| PRE-EMERGENCE | | | | | | | | | | | | | | |
| Morningglory | 5C,9G | 4C,7G | 3H | 9C | 9G | 8G | 2C,5H | 0 | 1C | 0 | 0 | 0 | 2C | 0 |
| Cocklebur | — | 0 | 5H | 9H | 8H | 0 | 0 | 0 | 0 | 0 | 0 | 0 | 0 | 0 |
| Sicklepod | 4C,8G | 4C,6G | 3G | 9G | — | 8G | 2C | 0 | 0 | 0 | 0 | — | 0 | 0 |
| Nutsedge | 10E | 0 | 0 | 10E | 10E | 0 | 10E | 0 | 0 | 0 | 0 | 0 | 0 | 0 |
| Crabgrass | 6G | 2C,5G | 2C,3G | 4G | 3G | 0 | 0 | 0 | 0 | 0 | 0 | 0 | 0 | 0 |
| Barnyardgrass | 4C,9H | 2C,5G | 0 | 4C,9H | 3C,8H | 3G | 0 | 0 | 0 | 0 | 0 | 0 | 0 | 0 |
| Wild Oats | 4C,8G | 2C,3G | 0 | 2C,6G | 1C,3G | 2G | 0 | 0 | 0 | 0 | 0 | 0 | 0 | 0 |
| Wheat | 8G | 3G | 0 | 2C,8H | 4G | 0 | 0 | 0 | 0 | 0 | 0 | 0 | 2G | 0 |
| Corn | 5C,9G | 4C,5G | 2C,2G | 2C,9H | 4C,9H | 2C | 2C | 0 | 3G | 0 | 0 | 0 | 3G | 0 |
| Soybean | 3C,5H | 2C,2H | 1C | 4C,7G | 3C,3H | 0 | 2C,3H | 0 | 0 | 0 | 0 | 0 | 1C | 0 |
| Rice | 3C,8H | 2C,5G | 0 | 10E | 4C,9H | 2C | 0 | 0 | 0 | 0 | 0 | 0 | 2C | 0 |
| Sorghum | 3C,9H | 3C,8G | 2C,3G | 6G,9H | 4C,9G | 2C,3H | 4C,5G | 0 | 0 | 0 | 0 | 0 | 2C,5G | 2C,6G |
| Sugar beet | 4C,8G | 3C,8G | 2C,4G | 5C,9G | 9G | 7G | 3C,8G | 2C | 2C,3G | 0 | 0 | 0 | 0 | 0 |
| Cotton | 2C | 0 | 0 | 9G | 2C,8G | 0 | 4G | 0 | 0 | 0 | 0 | 0 | 0 | 0 |

| | Cmpd. 8 | Cmpd. 9 | Compound 10 | | Cmpd. 11 | Cmpd. 12 | | Cmpd. 13 | Cmpd. 14 | Compound 15 | | Compound 16 | |
|---|---|---|---|---|---|---|---|---|---|---|---|---|---|
| Rate (kg/ha) | 0.4 | 0.4 | 0.4 | 0.05 | 0.4 | 0.4 | 2.0 | 0.4 | 0.4 | 0.4 | 2.0 | 0.4 | 2.0 |
| POSTEMERGENCE | | | | | | | | | | | | | |
| Morningglory | 3C,5G | 2C,3H | 4C,5G | 8G,2C | 3C,7H | 1C | 0 | 2C,9G | 5C,9G | 1C | 0 | 0 | 0 |
| Cocklebur | 0 | 0 | 1H | 0 | 4C,9H | 2C,5G | 6H | 0 | 5C,9G | 3C,8H | 2C,7H | 0 | 0 |
| Nutsedge | 0 | 0 | 2C,8G | 2C,5G | 0 | 0 | 0 | 3G | 5G | 0 | 0 | 0 | 0 |
| Crabgrass | 0 | 0 | 4H | 0 | 0 | 0 | 0 | 2G | 4G | 0 | 0 | 0 | 0 |
| Barnyardgrass | 0 | 0 | 1H | 0 | 0 | 0 | 0 | 2H | 2G | 0 | 0 | 0 | 0 |
| Wild Oats | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 2G | 0 | 0 | 0 | 0 |
| Corn | 0 | 0 | 0 | 0 | 0 | 0 | 0 | 2H | 2C,8H | 0 | 2H | 0 | 0 |
| Soybean | 3C,6G | 3C,7G | 3C,8G | 2C,9G | 3C,8G | 0 | 2C,5G | 3C,9G | 4C,9G | 0 | 0 | 0 | 0 |
| Rice | 4G | 3G | 2C,3G | 2G | 0 | 0 | 0 | 3C,9G | 2C,8H | 0 | 0 | 0 | 0 |
| Sorghum | 3G | 3C,5H | 2C,2H | 0 | 0 | 0 | 0 | 2C,9H | 3C,9G | 0 | 0 | 0 | 0 |
| Sugar Beets | 3C,6G | 2C | 5C,8H | 1C,4G | 2C,2G | 0 | 2H | 9C | 9C | 0 | 0 | 0 | 0 |
| Cotton | 0 | 0 | 3C,7G | 2C,5G | 3G | 0 | 0 | 4C,9G | 3C,8G | 0 | 2H | 0 | 0 |
| Cassia | 1C | 0 | 2C,5G | 0 | 2C | 0 | — | 2C,3G | 4C,6G | 0 | 0 | 0 | — |
| PREEMERGENCE | | | | | | | | | | | | | |
| Morningglory | 0 | 0 | 9G | 7G | 8G | 0 | 4H | 2C,8H | 9G | 1C | 7G | 0 | 0 |
| Cocklebur | 0 | 0 | 2G | 0 | 3C,6G | 0 | 3H | 0 | 9H | 2C,5H | 5H | 0 | 0 |
| Nutsedge | 0 | 0 | 8G | 5G | 0 | 0 | 0 | 2G | 2G | 0 | 0 | 0 | 0 |
| Crabgrass | 0 | 0 | 2G | 0 | 0 | 0 | 0 | 0 | 0 | 0 | 0 | 0 | 0 |
| Barnyardgrass | 0 | 0 | 4G | 1C | 0 | 0 | 0 | 6H | 5H | 0 | 0 | 0 | 0 |
| Wild Oats | 0 | 0 | 2G | 0 | 0 | 0 | 0 | 2C,4G | 2G | 0 | 0 | 0 | 0 |
| Wheat | 0 | 0 | 0 | 0 | 0 | 0 | 0 | 8G | 4G | 0 | 0 | 0 | 0 |
| Corn | 0 | 0 | 2C,8H | 2C,5G | 2C,4G | 0 | 0 | 2C,8G | 9G | 0 | 0 | 0 | 0 |
| Soybean | 0 | 0 | 2C | 0 | 0 | 0 | 0 | 2C,3H | 2C,4H | 0 | 0 | 0 | 0 |
| Rice | 0 | 0 | 4G | 2G | 0 | 0 | 0 | 3C,5G | 2C,2G | 0 | 0 | 0 | 0 |
| Sorghum | 0 | 0 | 2C,7G | 3G | 2C,3G | 0 | 0 | 2C,9H | 9H | 0 | 0 | 0 | 0 |
| Sugar Beets | 0 | 0 | 9G | 4G | 8G | 0 | 4H | 5C,9G | 5C,9G | 0 | 0 | 0 | 0 |
| Cotton | 0 | 0 | 5G | 0 | 0 | 0 | 0 | 2C,4G | 5G | 0 | 0 | 0 | 0 |
| Cassia | 0 | 0 | 2C,7G | 0 | 0 | 0 | — | 1C | 3C,5G | 0 | — | 0 | — |

What is claimed is:

1. A compound of formula:

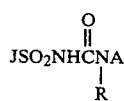

wherein J is

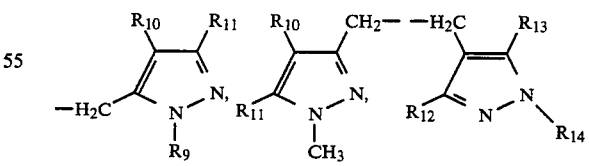

R is H or CH$_3$;

R$_9$ is H, C$_1$–C$_3$ alkyl or phenyl;

R$_{10}$ is CO$_2$R$_{15}$, C(O)NR$_{16}$R$_{17}$, SO$_2$NR$_{16}$R$_{17}$, SO$_2$N(OCH$_3$)CH$_3$, SO$_2$R$_{18}$ or NO$_2$;

R$_{11}$ is H or CH$_3$;

R$_{12}$ is H, CO$_2$R$_{15}$, C(O)NR$_{16}$R$_{17}$, SO$_2$NR$_{16}$R$_{17}$, SO$_2$N(OCH$_3$)CH$_3$, SO$_2$R$_{18}$ or NO$_2$;

$R_{13}$ is H, $CO_2R_{15}$, $C(O)NR_{16}R_{17}$, $SO_2NR_{16}R_{17}$, $SO_2N(OCH_3)CH_3$, $SO_2R_{18}$ or $NO_2$;

$R_{14}$ is H or $CH_3$;

$R_{15}$ is $C_1$–$C_2$ alkyl;

$R_{16}$ is H or $C_1$–$C_2$ alkyl;

$R_{17}$ is H or $C_1$–$C_2$ alkyl;

$R_{18}$ is $C_1$–$C_2$ alkyl;

A is

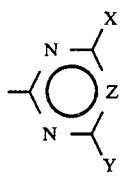

X is $CH_3$, $OCH_3$, Cl, Br, $OCH_2CF_3$ or $OCHF_2$;

Y is $C_1$–$C_3$ alkyl, $CH_2F$, cyclopropyl, $C\equiv CH$, $OCH_3$, $OC_2H_5$, $CH_2OCH_3$, $NH_2$, $NHCH_3$, $N(CH_3)_2$, $OCH_2CH_2F$, $CF_3$, $SCH_3$, $OCH_2CH=CH_2$, $OCH_2C\equiv CH$, $OCH_2CH_2OCH_3$, $CR(OCH_3)_2$,

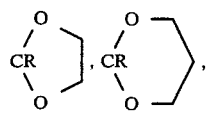

$CR(OCH_2CH_3)_2$ or $OCF_2H$;

Z is CH;

provided that (1) when X is Cl or Br, then Y is $OCH_3$, $OC_2H_5$, $NHCH_3$, $N(CH_3)_2$ or $OCF_2H$;

(2) $R_{12}$ and $R_{13}$ are not simultaneously H; and (3) when $R_{12}$ is other than H, then $R_{13}$ must be H.

2. Compounds of claim 1 where R is H, X is $CH_3$ or $OCH_3$ and Y is $C_1$–$C_2$ alkyl or $C_1$–$C_2$ alkoxy.

3. Compounds of claim 2 where J is J-4.

4. Compounds of claim 2 where J is J-5.

5. Compounds of claim 2 where J is J-6.

6. The compound of claim 1 which is 3-[[(4,6-dimethoxypyrimidin-2-yl)aminocarbonyl]aminosulfonylmethyl]-1,5-dimethyl-1H-pyrazole-4-carboxylic acid, ethyl ester.

7. The compound of claim 1 which is 5-[[(4,6-dimethoxypyrimidin-2-yl)aminocarbonyl]aminosulfonylmethyl]-1,3-dimethyl-1H-pyrazole-4-carboxylic acid, ethyl ester.

8. A composition suitable for controlling the growth of undesired vegetation which comprises an effective amount of a compound of claim 1 and at least one of the following: surfactant, solid or liquid diluent.

9. A composition suitable for controlling the growth of undesired vegetation which comprises an effective amount of a compound of claim 2 and at least one of the following: surfactant, solid or liquid diluent.

10. A composition suitable for controlling the growth of undesired vegetation which comprises an effective amount of a compound of claim 3 and at least one of the following: surfactant, solid or liquid diluent.

11. A composition suitable for controlling the growth of undesired vegetation which comprises an effective amount of a compound of claim 4 and at least one of the following: surfactant, solid or liquid diluent.

12. A composition suitable for controlling the growth of undesired vegetation which comprises an effective amount of a compound of claim 5 and at least one of the following: surfactant, solid or liquid diluent.

13. A composition suitable for controlling the growth of undesired vegetation which comprises an effective amount of the compound of claim 6 and at least one of the following: surfactant, solid or liquid diluent.

14. A composition suitable for controlling the growth of undesired vegetation which comprises an effective amount of the compound of claim 7 and at least one of the following: surfactant, solid or liquid diluent.

15. A method for controlling the growth of undesired vegetation which comprises applying to the locus to be protected an effective amount of a compound of claim 1.

16. A method for controlling the growth of undesired vegetation which comprises applying to the locus to be protected an effective amount of a compound of claim 2.

17. A method for controlling the growth of undesired vegetation which comprises applying to the locus to be protected an effective amount of a compound of claim 3.

18. A method for controlling the growth of undesired vegetation which comprises applying to the locus to be protected an effective amount of a compound of claim 4.

19. A method for controlling the growth of undesired vegetation which comprises applying to the locus to be protected an effective amount of a compound of claim 5.

20. A method for controlling the growth of undesired vegetation which comprises applying to the locus to be protected an effective amount of the compound of claim 6.

21. A method for controlling the growth of undesired vegetation which comprises applying to the locus to be protected an effective amount of the compound of claim 7.

* * * * *